United States Patent
Mashiach

(10) Patent No.: US 10,918,376 B2
(45) Date of Patent: Feb. 16, 2021

(54) THERAPY PROTOCOL ACTIVATION TRIGGERED BASED ON INITIAL COUPLING

(71) Applicant: Adi Mashiach, Tel Aviv (IL)

(72) Inventor: Adi Mashiach, Tel Aviv (IL)

(73) Assignee: Nyxoah SA, Mont-St-Guibert (BE)

( * ) Notice: Subject to any disclaimer, the term of this patent is extended or adjusted under 35 U.S.C. 154(b) by 0 days.

(21) Appl. No.: 13/952,150

(22) Filed: Jul. 26, 2013

(65) Prior Publication Data

US 2014/0031904 A1  Jan. 30, 2014

Related U.S. Application Data

(60) Provisional application No. 61/676,327, filed on Jul. 26, 2012.

(51) Int. Cl.
*A61B 17/04* (2006.01)
*A61N 1/36* (2006.01)
(Continued)

(52) U.S. Cl.
CPC ........ *A61B 17/0482* (2013.01); *A61N 1/0526* (2013.01); *A61N 1/0558* (2013.01);
(Continued)

(58) Field of Classification Search
CPC .............. A61N 1/3787; A61N 1/37211; A61N 1/3601; A61N 1/3606; A61N 1/0492;
(Continued)

(56) References Cited

U.S. PATENT DOCUMENTS

| | | |
|---|---|---|
| 4,905,011 A | 2/1990 | Shea |
| 5,540,732 A | 7/1996 | Testerman |
| | (Continued) | |

FOREIGN PATENT DOCUMENTS

| | | |
|---|---|---|
| DE | 10003338 A1 | 11/2000 |
| DE | 69526767 T2 | 1/2003 |
| | (Continued) | |

OTHER PUBLICATIONS

Timothy Wagner et al., Noninvasive Human Brain Stimulation, Annu. Rev. Biomed. Eng. 2007, pp. 527-565.
(Continued)

*Primary Examiner* — Christopher A Flory
*Assistant Examiner* — Minh Duc G Pham
(74) *Attorney, Agent, or Firm* — Finnegan, Henderson, Farabow, Garrett & Dunner, LLP

(57) ABSTRACT

The present disclosure is directed to a control unit for cooperating with an adhesive patch to convey power from a location external to a subject to a location within the subject. The control unit may include a housing configured for selective mounting on the adhesive patch and may further include at least one processor within the housing. The at least one processor may be configured to activate when the housing is mounted on the adhesive patch and to delay, for a predetermined amount of time following activation of the at least one processor, generation of therapeutic control signals for modulating at least one nerve in the subject's body.

7 Claims, 11 Drawing Sheets

(51) Int. Cl.
  *A61N 1/05* (2006.01)
  *A61N 1/372* (2006.01)
  *H02J 50/12* (2016.01)
  *A61N 1/378* (2006.01)
  *H04B 5/00* (2006.01)
  *H02J 7/02* (2016.01)
  *H02J 50/05* (2016.01)

(52) U.S. Cl.
  CPC ....... *A61N 1/3601* (2013.01); *A61N 1/36003* (2013.01); *A61N 1/3606* (2013.01); *A61N 1/3611* (2013.01); *A61N 1/36071* (2013.01); *A61N 1/36117* (2013.01); *A61N 1/36125* (2013.01); *A61N 1/36189* (2013.01); *A61N 1/3787* (2013.01); *A61N 1/37229* (2013.01); *H02J 7/025* (2013.01); *H02J 50/12* (2016.02); *H04B 5/0037* (2013.01); *H02J 50/05* (2016.02); *H04B 5/0031* (2013.01); *H04B 5/0081* (2013.01); *H04B 5/0093* (2013.01); *Y10T 29/49018* (2015.01)

(58) Field of Classification Search
  CPC .... A61N 1/36014; A61N 1/02; A61B 5/4818; A61B 5/6833
  USPC .............................................. 607/42, 59, 62
  See application file for complete search history.

(56) References Cited

U.S. PATENT DOCUMENTS

| | | |
|---|---|---|
| 5,540,733 A | 7/1996 | Testerman et al. |
| 5,546,952 A | 8/1996 | Erickson |
| 5,549,655 A | 8/1996 | Erickson |
| 5,571,148 A | 11/1996 | Loeb et al. |
| 5,591,216 A | 1/1997 | Testerman et al. |
| 5,690,693 A | 11/1997 | Wang et al. |
| 5,702,431 A | 12/1997 | Wang et al. |
| 5,725,564 A | 3/1998 | Freed et al. |
| 5,741,316 A | 4/1998 | Chen et al. |
| 5,871,512 A | 2/1999 | Hemming et al. |
| 5,873,898 A | 2/1999 | Hemming et al. |
| 5,891,185 A | 4/1999 | Freed et al. |
| 5,945,762 A | 8/1999 | Chen et al. |
| 5,948,006 A * | 9/1999 | Mann ................ A61N 1/37235 607/61 |
| 5,987,359 A | 11/1999 | Freed et al. |
| 6,009,878 A | 1/2000 | Weijand et al. |
| 6,038,480 A | 3/2000 | Hrdlicka et al. |
| 6,051,017 A | 4/2000 | Loeb et al. |
| 6,058,330 A | 5/2000 | Borza |
| 6,092,531 A | 7/2000 | Chen et al. |
| 6,104,958 A | 8/2000 | Freed et al. |
| 6,132,384 A | 10/2000 | Christopherson et al. |
| 6,134,473 A | 10/2000 | Hemming et al. |
| 6,144,881 A | 11/2000 | Hemming et al. |
| 6,163,724 A | 12/2000 | Hemming et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,198,970 B1 | 3/2001 | Freed et al. |
| 6,212,431 B1 | 4/2001 | Hahn et al. |
| 6,212,435 B1 | 4/2001 | Lattner et al. |
| 6,214,032 B1 | 4/2001 | Loeb et al. |
| 6,240,316 B1 | 5/2001 | Richmond et al. |
| 6,240,318 B1 | 5/2001 | Phillips |
| 6,251,126 B1 | 6/2001 | Ottenhoff et al. |
| 6,269,269 B1 | 7/2001 | Ottenhoff et al. |
| 6,275,737 B1 | 8/2001 | Mann |
| 6,281,611 B1 | 8/2001 | Chen et al. |
| 6,305,381 B1 | 10/2001 | Weijand et al. |
| 6,324,430 B1 | 11/2001 | Zarinetchi et al. |
| 6,324,431 B1 | 11/2001 | Zarinetchi et al. |
| 6,331,744 B1 | 12/2001 | Chen et al. |
| 6,344,021 B1 | 2/2002 | Juster et al. |
| 6,345,202 B2 | 2/2002 | Richmond et al. |
| 6,358,281 B1 | 3/2002 | Berrang et al. |
| 6,389,318 B1 | 5/2002 | Zarinetchi et al. |
| 6,430,444 B1 | 8/2002 | Borza |
| 6,473,653 B1 | 10/2002 | Schallhorn et al. |
| 6,477,425 B1 | 11/2002 | Nowick et al. |
| 6,496,733 B2 | 12/2002 | Zarinetchi et al. |
| 6,505,074 B2 | 1/2003 | Boveja et al. |
| 6,572,543 B1 | 6/2003 | Christopherson et al. |
| 6,574,507 B1 | 6/2003 | Bonnet |
| 6,587,725 B1 | 7/2003 | Durand et al. |
| 6,622,049 B2 | 9/2003 | Penner et al. |
| 6,628,989 B1 | 9/2003 | Penner et al. |
| 6,636,767 B1 | 10/2003 | Knudson et al. |
| 6,648,914 B2 | 11/2003 | Berrang et al. |
| 6,657,351 B2 | 12/2003 | Chen et al. |
| 6,684,105 B2 | 1/2004 | Cohen et al. |
| 6,704,602 B2 | 3/2004 | Berg et al. |
| 6,735,475 B1 | 5/2004 | Whitehurst et al. |
| 6,736,771 B2 | 5/2004 | Sokolich et al. |
| 6,738,671 B2 | 5/2004 | Christopherson et al. |
| 6,764,446 B2 | 7/2004 | Wolinsky et al. |
| 6,770,022 B2 | 8/2004 | Mechlenburg et al. |
| 6,788,975 B1 | 9/2004 | Whitehurst et al. |
| 6,839,594 B2 | 1/2005 | Cohen et al. |
| 6,845,271 B2 | 1/2005 | Fang et al. |
| 6,850,803 B1 | 2/2005 | Jimenez et al. |
| 6,892,098 B2 | 5/2005 | Ayal et al. |
| 6,907,295 B2 | 6/2005 | Gross et al. |
| 6,928,324 B2 | 8/2005 | Park et al. |
| 6,937,891 B2 | 8/2005 | Leinders et al. |
| 7,024,248 B2 | 4/2006 | Penner et al. |
| 7,027,860 B2 | 4/2006 | Bruninga et al. |
| 7,039,468 B2 | 5/2006 | Freed et al. |
| 7,054,691 B1 | 5/2006 | Kuzma et al. |
| 7,103,408 B2 | 9/2006 | Haller et al. |
| 7,120,992 B2 | 10/2006 | He et al. |
| 7,132,173 B2 | 11/2006 | Daulton |
| 7,146,221 B2 | 12/2006 | Krulevitch et al. |
| 7,149,586 B2 | 12/2006 | Greenberg et al. |
| 7,155,278 B2 | 12/2006 | King et al. |
| 7,167,737 B2 | 1/2007 | Fujii et al. |
| 7,177,698 B2 | 2/2007 | Klosterman et al. |
| 7,181,287 B2 | 2/2007 | Greenberg |
| 7,198,603 B2 | 4/2007 | Penner et al. |
| 7,209,790 B2 | 4/2007 | Thompson et al. |
| 7,212,862 B2 | 5/2007 | Park et al. |
| 7,225,032 B2 | 5/2007 | Schmeling et al. |
| 7,257,438 B2 | 8/2007 | Kinast |
| 7,263,403 B2 | 8/2007 | Greenberg et al. |
| 7,273,457 B2 | 9/2007 | Penner |
| 7,277,749 B2 | 10/2007 | Gordon et al. |
| 7,280,873 B2 | 10/2007 | Freed et al. |
| 7,283,874 B2 | 10/2007 | Penner |
| 7,286,881 B2 | 10/2007 | Schommer et al. |
| 7,289,855 B2 | 10/2007 | Nghiem et al. |
| 7,308,316 B2 | 12/2007 | Schommer |
| 7,317,947 B2 | 1/2008 | Wahlstrand et al. |
| 7,321,793 B2 | 1/2008 | Ben Ezra et al. |
| 7,324,853 B2 | 1/2008 | Ayal et al. |
| 7,338,522 B2 | 3/2008 | Greenberg et al. |
| 7,341,562 B2 | 3/2008 | Pless et al. |
| 7,346,398 B2 | 3/2008 | Gross et al. |
| 7,351,921 B1 | 4/2008 | Haller et al. |
| 7,367,935 B2 | 5/2008 | Mechlenburg et al. |
| 7,392,091 B2 | 6/2008 | Bruinsma |
| 7,392,092 B2 | 6/2008 | Li et al. |
| 7,409,245 B1 | 8/2008 | Larson et al. |
| 7,428,438 B2 | 9/2008 | Parramon et al. |
| 7,437,193 B2 | 10/2008 | Parramon et al. |
| 7,447,551 B2 | 11/2008 | Kuo et al. |
| 7,482,783 B2 | 1/2009 | Schommer |
| 7,483,750 B2 | 1/2009 | Greenberg et al. |
| 7,489,966 B2 | 2/2009 | Leinders et al. |
| 7,493,172 B2 | 2/2009 | Whitehurst et al. |
| 7,499,754 B2 | 3/2009 | Greenberg et al. |
| 7,502,652 B2 | 3/2009 | Gaunt et al. |
| 7,512,443 B2 | 3/2009 | Phillips et al. |

(56) References Cited

U.S. PATENT DOCUMENTS

| | | |
|---|---|---|
| 7,527,621 B2 | 5/2009 | Greenberg et al. |
| 7,555,345 B2 | 6/2009 | Wahlstrand et al. |
| 7,561,922 B2 | 7/2009 | Cohen et al. |
| 7,587,241 B2 | 9/2009 | Parramon et al. |
| 7,599,744 B2 | 10/2009 | Giordano et al. |
| 7,610,065 B2 | 10/2009 | Vallapureddy et al. |
| 7,610,103 B2 | 10/2009 | Whitehurst et al. |
| 7,617,001 B2 | 11/2009 | Penner et al. |
| 7,628,750 B2 | 12/2009 | Cohen et al. |
| 7,630,771 B2 | 12/2009 | Cauller |
| 7,631,424 B2 | 12/2009 | Greenberg et al. |
| 7,634,317 B2 | 12/2009 | Ben-David et al. |
| 7,636,602 B2 | 12/2009 | Baru Fassio et al. |
| 7,640,061 B2 | 12/2009 | He et al. |
| 7,641,619 B2 | 1/2010 | Penner |
| 7,647,112 B2 | 1/2010 | Tracey et al. |
| 7,660,632 B2 | 2/2010 | Kirby et al. |
| 7,668,580 B2 | 2/2010 | Shin et al. |
| 7,668,602 B2 | 2/2010 | Ben-David et al. |
| 7,672,728 B2 | 3/2010 | Libbus et al. |
| 7,680,538 B2 | 3/2010 | Durand et al. |
| 7,684,866 B2 | 3/2010 | Fowler et al. |
| 7,711,435 B2 | 5/2010 | Schommer |
| 7,720,547 B2 | 5/2010 | Denker et al. |
| 7,725,195 B2 | 5/2010 | Lima et al. |
| 7,734,355 B2 | 6/2010 | Cohen et al. |
| 7,756,587 B2 | 7/2010 | Penner et al. |
| 7,764,988 B2 | 7/2010 | Drew et al. |
| 7,766,216 B2 | 8/2010 | Daulton |
| 7,769,461 B2 | 8/2010 | Whitehurst et al. |
| 7,774,069 B2 | 8/2010 | Olson et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,781,683 B2 | 8/2010 | Haller et al. |
| 7,782,192 B2 * | 8/2010 | Jeckelmann ...... A61M 5/14276 340/539.12 |
| 7,797,050 B2 | 9/2010 | Libbus et al. |
| 7,805,203 B2 | 9/2010 | Ben-David et al. |
| 7,809,442 B2 | 10/2010 | Bolea et al. |
| 7,810,233 B2 | 10/2010 | Krulevitch et al. |
| 7,822,480 B2 | 10/2010 | Park et al. |
| 7,831,308 B2 | 11/2010 | Rezai et al. |
| 7,836,888 B2 | 11/2010 | Hegde et al. |
| 7,844,346 B2 | 11/2010 | Cohen et al. |
| 7,845,357 B2 | 12/2010 | Buscemi et al. |
| 7,848,817 B2 | 12/2010 | Janzig et al. |
| 7,881,800 B2 | 2/2011 | Daly et al. |
| 7,882,842 B2 | 2/2011 | Bhat et al. |
| 7,885,709 B2 | 2/2011 | Ben-David |
| 7,885,711 B2 | 2/2011 | Ben-Ezra et al. |
| 7,887,493 B2 | 2/2011 | Stahmann et al. |
| 7,890,178 B2 | 2/2011 | Testerman et al. |
| 7,890,185 B2 | 2/2011 | Cohen et al. |
| 7,890,193 B2 | 2/2011 | Tingey |
| 7,894,909 B2 | 2/2011 | Greenberg et al. |
| 7,904,151 B2 | 3/2011 | Ben-David et al. |
| 7,904,163 B2 | 3/2011 | Greenberg et al. |
| 7,904,167 B2 | 3/2011 | Klosterman et al. |
| 7,904,176 B2 | 3/2011 | Ben-Ezra et al. |
| 7,908,008 B2 | 3/2011 | Ben-David et al. |
| 7,909,037 B2 | 3/2011 | Hegde et al. |
| 7,909,038 B2 | 3/2011 | Hegde et al. |
| 7,925,356 B2 | 4/2011 | Li et al. |
| 7,930,031 B2 | 4/2011 | Penner |
| RE42,378 E | 5/2011 | Wolinsky et al. |
| 7,937,159 B2 | 5/2011 | Lima et al. |
| 7,945,334 B2 | 5/2011 | Jimenez et al. |
| 7,970,479 B2 | 6/2011 | Goroszeniuk |
| 7,973,722 B1 | 7/2011 | Hill et al. |
| 7,974,693 B2 | 7/2011 | Ben-David et al. |
| 7,979,126 B2 | 7/2011 | Payne et al. |
| 7,979,128 B2 | 7/2011 | Tehrani et al. |
| 7,979,137 B2 | 7/2011 | Tracey et al. |
| 7,980,248 B2 | 7/2011 | Hegde et al. |
| 7,991,478 B2 | 8/2011 | Greenberg et al. |
| 8,005,542 B2 | 8/2011 | Ben-Ezra et al. |
| 8,005,545 B2 | 8/2011 | Ben-David et al. |
| 8,010,205 B2 | 8/2011 | Rahman et al. |
| 8,014,878 B2 | 9/2011 | Greenberg et al. |
| 8,024,044 B2 | 9/2011 | Kirby et al. |
| 8,024,047 B2 | 9/2011 | Olson et al. |
| 8,027,735 B1 | 9/2011 | Tziviskos et al. |
| 8,032,227 B2 | 10/2011 | Parramon et al. |
| 8,035,255 B2 | 10/2011 | Kurs et al. |
| 8,036,745 B2 | 10/2011 | Ben-David et al. |
| 8,036,752 B2 | 10/2011 | Greenberg et al. |
| 8,060,197 B2 | 11/2011 | Ben-David et al. |
| 8,060,211 B2 | 11/2011 | Greenberg et al. |
| 8,065,021 B2 | 11/2011 | Gross et al. |
| 8,074,655 B2 | 12/2011 | Sanders |
| 8,078,278 B2 | 12/2011 | Penner |
| 8,078,284 B2 | 12/2011 | Greenberg et al. |
| 8,086,318 B2 | 12/2011 | Strother et al. |
| 8,115,618 B2 | 2/2012 | Robertson et al. |
| 8,116,881 B2 | 2/2012 | Cohen et al. |
| 8,122,596 B2 | 2/2012 | Krulevitch et al. |
| 8,126,562 B2 | 2/2012 | Fowler et al. |
| 8,127,424 B2 | 3/2012 | Haller et al. |
| 8,131,375 B2 | 3/2012 | Greenberg et al. |
| 8,140,167 B2 | 3/2012 | Donders et al. |
| 8,160,696 B2 | 4/2012 | Bendett et al. |
| 8,165,695 B2 | 4/2012 | DiUbaldi et al. |
| 8,170,680 B2 | 5/2012 | Ameri |
| 8,170,681 B2 | 5/2012 | Jimenez et al. |
| 8,174,460 B2 | 5/2012 | Larson et al. |
| 8,175,714 B2 | 5/2012 | Greenberg et al. |
| 8,175,716 B2 | 5/2012 | Rahman et al. |
| 8,180,460 B2 | 5/2012 | Nevsmith et al. |
| 8,185,212 B2 | 5/2012 | Carbunaru et al. |
| 8,204,591 B2 | 6/2012 | Ben-David et al. |
| 8,214,009 B2 | 7/2012 | Shin et al. |
| 8,214,045 B2 | 7/2012 | Kronich et al. |
| 8,220,467 B2 | 7/2012 | Sanders |
| 8,224,444 B2 | 7/2012 | Ben-David et al. |
| 8,224,449 B2 | 7/2012 | Carbunaru et al. |
| 8,229,567 B2 | 7/2012 | Phillips et al. |
| 8,238,975 B2 | 8/2012 | Vallapureddy et al. |
| 8,241,950 B2 | 8/2012 | Pellinen et al. |
| 8,249,713 B2 | 8/2012 | Fang et al. |
| 8,249,723 B2 | 8/2012 | McCreery |
| 8,256,425 B2 | 9/2012 | Bagley et al. |
| 8,260,422 B2 | 9/2012 | Ellingson et al. |
| 8,260,432 B2 | 9/2012 | DiGiore et al. |
| 8,260,439 B2 | 9/2012 | Diubaldi et al. |
| 8,265,763 B2 | 9/2012 | Fahey |
| 8,265,770 B2 | 9/2012 | Toy et al. |
| 8,285,381 B2 | 10/2012 | Fahey |
| 8,295,936 B2 | 10/2012 | Wahlstrand et al. |
| 8,301,261 B2 | 10/2012 | Bruinsma |
| 8,311,645 B2 | 11/2012 | Bolea et al. |
| 8,336,553 B2 | 12/2012 | Bhat et al. |
| 8,346,361 B2 | 1/2013 | Bauhahn et al. |
| 8,352,026 B2 | 1/2013 | DiUbaldi |
| 8,359,108 B2 | 1/2013 | McCreery |
| 8,369,957 B2 | 2/2013 | Greenberg et al. |
| 8,381,735 B2 | 2/2013 | Buscemi et al. |
| 8,386,046 B2 | 2/2013 | Tesfayesus et al. |
| 8,386,048 B2 | 2/2013 | McClure et al. |
| 8,386,056 B2 | 2/2013 | Ben David et al. |
| 8,391,991 B2 | 3/2013 | Rahman et al. |
| 8,406,886 B2 | 3/2013 | Gaunt et al. |
| 8,408,213 B2 | 4/2013 | Sanders |
| 8,417,343 B2 | 4/2013 | Bolea et al. |
| 8,428,725 B2 | 4/2013 | Meadows et al. |
| 8,428,727 B2 | 4/2013 | Bolea et al. |
| 8,428,746 B2 | 4/2013 | DiGiore et al. |
| 8,433,403 B2 | 4/2013 | Fahey |
| 8,447,410 B2 | 5/2013 | Greenberg et al. |
| 8,457,758 B2 | 6/2013 | Olson et al. |
| 8,463,383 B2 | 6/2013 | Sakai et al. |
| 8,463,394 B2 | 6/2013 | Forsell |
| 8,463,395 B2 | 6/2013 | Forsell |
| 8,473,025 B2 | 6/2013 | Shin et al. |

(56) References Cited

U.S. PATENT DOCUMENTS

| | | |
|---|---|---|
| 8,489,200 B2 | 7/2013 | Zarinetchi et al. |
| 8,494,641 B2 | 7/2013 | Boling et al. |
| 8,494,655 B2 | 7/2013 | Ayal et al. |
| 8,498,712 B2 | 7/2013 | Bolea et al. |
| 8,498,716 B2 | 7/2013 | Chen et al. |
| 8,509,909 B2 | 8/2013 | Figueiredo et al. |
| 8,509,911 B2 | 8/2013 | Li et al. |
| 8,510,939 B2 | 8/2013 | Greenberg et al. |
| 8,515,544 B2 | 8/2013 | Daly et al. |
| 8,532,787 B2 | 9/2013 | Lambert et al. |
| 8,538,503 B2 | 9/2013 | Kumar et al. |
| 8,540,631 B2 | 9/2013 | Penner et al. |
| 8,540,632 B2 | 9/2013 | Robertson et al. |
| 8,543,216 B2 | 9/2013 | Carbunaru et al. |
| 8,560,046 B2 | 10/2013 | Kumar et al. |
| 8,565,896 B2 | 10/2013 | Ben-David et al. |
| 8,571,651 B2 | 10/2013 | Ben-Ezra et al. |
| 8,571,653 B2 | 10/2013 | Ben-David et al. |
| 8,571,679 B2 | 10/2013 | Parramon et al. |
| 8,577,460 B2 | 11/2013 | Penner |
| 8,578,937 B2 | 11/2013 | Bhat et al. |
| 8,583,256 B2 | 11/2013 | Tracey et al. |
| 8,588,901 B2 | 11/2013 | Fahey |
| 8,588,924 B2 | 11/2013 | Dion |
| 8,588,930 B2 | 11/2013 | DiUbaldi et al. |
| 8,600,517 B2 | 12/2013 | Forsell |
| 8,612,013 B2 | 12/2013 | Forsell |
| 8,612,014 B2 | 12/2013 | Rahman et al. |
| 8,615,294 B2 | 12/2013 | Ben-David et al. |
| 8,620,437 B2 | 12/2013 | Wahlstrand et al. |
| 8,620,447 B2 | 12/2013 | D'Ambrosio et al. |
| 8,626,302 B2 | 1/2014 | Bennett et al. |
| 8,626,304 B2 | 1/2014 | Bolea et al. |
| 8,639,344 B2 | 1/2014 | Greenberg et al. |
| 8,639,354 B2 | 1/2014 | Bolea et al. |
| 8,644,939 B2 | 2/2014 | Wilson et al. |
| 8,655,451 B2 | 2/2014 | Klosterman et al. |
| 8,657,756 B2 | 2/2014 | Stahmann et al. |
| 8,658,465 B2 | 2/2014 | Pellinen et al. |
| 8,668,643 B2 | 3/2014 | Kinast |
| 8,670,835 B2 | 3/2014 | Park et al. |
| 8,676,332 B2 | 3/2014 | Fahey |
| 8,700,177 B2 | 4/2014 | Strother et al. |
| 8,703,537 B2 | 4/2014 | Pellinen et al. |
| 8,718,758 B2 | 5/2014 | Wagner et al. |
| 8,718,783 B2 | 5/2014 | Bolea et al. |
| 8,718,791 B2 | 5/2014 | Ben-David et al. |
| 8,725,271 B2 | 5/2014 | Ayal et al. |
| 8,738,148 B2 | 5/2014 | Olson et al. |
| 8,744,582 B2 | 6/2014 | Wahlstrand et al. |
| 8,744,589 B2 | 6/2014 | Bolea et al. |
| 8,751,003 B2 | 6/2014 | DiUbaldi et al. |
| 8,751,005 B2 | 6/2014 | Meadows et al. |
| 8,774,943 B2 | 7/2014 | McCreery |
| 8,788,046 B2 | 7/2014 | Bennett et al. |
| 8,788,047 B2 | 7/2014 | Bennett et al. |
| 8,788,048 B2 | 7/2014 | Bennett et al. |
| 8,798,763 B2 | 8/2014 | Forsell |
| 8,813,753 B2 | 8/2014 | Bhat et al. |
| 8,825,173 B2 | 9/2014 | Forsell |
| 8,855,771 B2 | 10/2014 | Tesfayesus et al. |
| 8,862,232 B2 | 10/2014 | Zarinetchi et al. |
| 8,880,184 B2 | 11/2014 | Phillips et al. |
| 8,886,304 B2 | 11/2014 | Wagner et al. |
| 8,886,322 B2 | 11/2014 | Meadows et al. |
| 8,886,325 B2 | 11/2014 | Boling et al. |
| 8,886,329 B2 | 11/2014 | Greenberg et al. |
| 8,886,337 B2 | 11/2014 | Bennett et al. |
| 8,892,200 B2 | 11/2014 | Wagner et al. |
| 8,892,205 B2 | 11/2014 | Miller, III et al. |
| 8,892,210 B2 | 11/2014 | Fahey |
| 8,897,871 B2 | 11/2014 | Wagner et al. |
| 8,903,495 B2 | 12/2014 | Greenberg et al. |
| 8,903,502 B2 | 12/2014 | Perryman et al. |
| 8,914,129 B2 | 12/2014 | Parramon et al. |
| 8,925,551 B2 | 1/2015 | Sanders |
| 8,929,979 B2 | 1/2015 | Wagner et al. |
| 8,929,986 B2 | 1/2015 | Parker et al. |
| 8,934,972 B2 | 1/2015 | Penner |
| 8,954,153 B2 | 2/2015 | Boggs, II |
| 8,965,523 B2 | 2/2015 | Forsell |
| 8,965,525 B2 | 2/2015 | Forsell |
| 8,965,535 B2 | 2/2015 | Dunlay et al. |
| 8,972,021 B2 | 3/2015 | Edgell et al. |
| 8,977,354 B2 | 3/2015 | Wagner et al. |
| 8,983,611 B2 | 3/2015 | Mokelke et al. |
| 9,002,451 B2 | 4/2015 | Staunton et al. |
| 9,026,222 B2 | 5/2015 | Forsell |
| 9,031,654 B2 | 5/2015 | Meadows et al. |
| 9,042,991 B2 | 5/2015 | Reed et al. |
| 9,061,134 B2 | 6/2015 | Askin, III et al. |
| 9,072,886 B2 | 7/2015 | Gaunt et al. |
| 9,079,041 B2 | 7/2015 | Park et al. |
| 9,079,043 B2 | 7/2015 | Stark et al. |
| 9,089,690 B2 | 7/2015 | Greenberg et al. |
| 9,113,838 B2 | 8/2015 | Tesfayesus et al. |
| 9,125,290 B2 | 9/2015 | Greenberg et al. |
| 9,126,039 B2 | 9/2015 | Fahey |
| 9,149,228 B2 | 10/2015 | Kinast |
| 9,149,386 B2 | 10/2015 | Fahey et al. |
| 9,149,628 B2 | 10/2015 | Wahlstrand et al. |
| 9,162,071 B2 | 10/2015 | Parramon et al. |
| 9,186,496 B2 | 11/2015 | Greenberg et al. |
| 9,186,511 B2 | 11/2015 | Bolea |
| 9,205,258 B2 | 12/2015 | Simon et al. |
| 9,205,262 B2 | 12/2015 | Bolea et al. |
| 9,227,076 B2 | 1/2016 | Sharma et al. |
| 9,233,258 B2 | 1/2016 | Simon et al. |
| 9,241,649 B2 | 1/2016 | Kumar et al. |
| 9,242,106 B2 | 1/2016 | Klosterman et al. |
| 9,248,289 B2 | 2/2016 | Bennett et al. |
| 9,272,081 B2 | 3/2016 | Cameron et al. |
| 9,289,142 B2 | 3/2016 | Kong et al. |
| 9,302,104 B2 | 4/2016 | Fahey |
| 9,308,370 B2 | 4/2016 | Lima et al. |
| 9,314,615 B2 | 4/2016 | Neysmith et al. |
| 9,314,618 B2 | 4/2016 | Imran et al. |
| 9,314,641 B2 | 4/2016 | Meadows et al. |
| 9,320,895 B2 | 4/2016 | Wagner et al. |
| 9,320,908 B2 | 4/2016 | Fletcher et al. |
| 9,339,647 B2 | 5/2016 | Strother et al. |
| 9,339,651 B2 | 5/2016 | Meadows et al. |
| 2001/0010010 A1 | 7/2001 | Richmond et al. |
| 2002/0010495 A1 | 1/2002 | Freed et al. |
| 2002/0038138 A1 | 3/2002 | Zarinetchi et al. |
| 2002/0055763 A1 | 5/2002 | Zarinetchi et al. |
| 2002/0058971 A1 | 5/2002 | Zarinetchi et al. |
| 2002/0077572 A1 | 6/2002 | Fang et al. |
| 2002/0177884 A1 | 11/2002 | Ahn et al. |
| 2002/0188333 A1 | 12/2002 | Nowick et al. |
| 2003/0030342 A1 | 2/2003 | Chen et al. |
| 2003/0030593 A1 | 2/2003 | Tomomatsu et al. |
| 2003/0093128 A1 | 5/2003 | Freed et al. |
| 2003/0097165 A1 | 5/2003 | Krulevitch et al. |
| 2003/0195571 A1 | 10/2003 | Burnes et al. |
| 2004/0064166 A1 | 4/2004 | Thompson et al. |
| 2004/0073272 A1 | 4/2004 | Knudson et al. |
| 2004/0098068 A1 | 5/2004 | Carbunaru et al. |
| 2004/0172104 A1 | 9/2004 | Berg et al. |
| 2004/0199212 A1* | 10/2004 | Fischell ............ A61N 1/37258 607/32 |
| 2004/0236387 A1 | 11/2004 | Fang et al. |
| 2005/0065553 A1 | 3/2005 | Ben Ezra et al. |
| 2005/0085874 A1 | 4/2005 | Davis et al. |
| 2005/0102006 A1 | 5/2005 | Whitehurst et al. |
| 2005/0177067 A1 | 8/2005 | Tracey et al. |
| 2005/0267547 A1 | 12/2005 | Knudson et al. |
| 2005/0288743 A1 | 12/2005 | Ahn et al. |
| 2006/0009816 A1 | 1/2006 | Fang et al. |
| 2006/0064140 A1 | 3/2006 | Whitehurst et al. |
| 2006/0090762 A1 | 5/2006 | Hegde et al. |
| 2006/0116739 A1 | 6/2006 | Betser et al. |
| 2006/0190056 A1 | 8/2006 | Fowler et al. |
| 2006/0241717 A1 | 10/2006 | Whitehurst et al. |

(56) References Cited

U.S. PATENT DOCUMENTS

| | | |
|---|---|---|
| 2006/0270968 A1 | 11/2006 | Greenberg et al. |
| 2007/0055324 A1 | 3/2007 | Thompson et al. |
| 2007/0144535 A1 | 6/2007 | Hegde et al. |
| 2007/0173893 A1 | 7/2007 | Pitts |
| 2007/0205291 A1 | 9/2007 | Aramaki et al. |
| 2007/0233204 A1 | 10/2007 | Lima et al. |
| 2007/0261701 A1 | 11/2007 | Sanders |
| 2008/0046016 A1 | 2/2008 | Ben-David et al. |
| 2008/0047566 A1 | 2/2008 | Hegde et al. |
| 2008/0057179 A1 | 3/2008 | Greenberg et al. |
| 2008/0058898 A1 | 3/2008 | Greenberg et al. |
| 2008/0064946 A1 | 3/2008 | Greenberg et al. |
| 2008/0078411 A1 | 4/2008 | Buscemi et al. |
| 2008/0078412 A1 | 4/2008 | Buscemi et al. |
| 2008/0091241 A1 | 4/2008 | Ben-Ezra et al. |
| 2008/0091245 A1 | 4/2008 | Ben-Ezra et al. |
| 2008/0103545 A1* | 5/2008 | Bolea ............... A61N 1/3606 607/42 |
| 2008/0109045 A1 | 5/2008 | Gross et al. |
| 2008/0109046 A1* | 5/2008 | Lima ................. A61N 1/0551 607/42 |
| 2008/0119898 A1 | 5/2008 | Ben-David et al. |
| 2008/0125819 A1 | 5/2008 | Ben-David et al. |
| 2008/0125827 A1 | 5/2008 | Ben-David et al. |
| 2008/0132964 A1 | 6/2008 | Cohen et al. |
| 2008/0147137 A1 | 6/2008 | Cohen et al. |
| 2008/0177351 A1 | 7/2008 | Fang et al. |
| 2008/0300657 A1 | 12/2008 | Stultz |
| 2009/0005845 A1 | 1/2009 | David et al. |
| 2009/0038623 A1 | 2/2009 | Farbarik et al. |
| 2009/0069866 A1 | 3/2009 | Farbarik et al. |
| 2009/0078274 A1 | 3/2009 | Bhat et al. |
| 2009/0078275 A1 | 3/2009 | Hegde et al. |
| 2009/0131995 A1 | 5/2009 | Sloan et al. |
| 2009/0173351 A1 | 7/2009 | Sahin et al. |
| 2009/0240314 A1 | 9/2009 | Kong et al. |
| 2010/0010603 A1 | 1/2010 | Ben-David et al. |
| 2010/0016929 A1 | 1/2010 | Prochazka |
| 2010/0063568 A1 | 3/2010 | Staunton et al. |
| 2010/0069994 A1 | 3/2010 | Cauller |
| 2010/0131029 A1 | 5/2010 | Durand et al. |
| 2010/0152809 A1 | 6/2010 | Boggs, II |
| 2010/0174341 A1 | 7/2010 | Bolea et al. |
| 2010/0198103 A1 | 8/2010 | Meadows et al. |
| 2010/0198306 A1* | 8/2010 | Lima et al. ................ 607/60 |
| 2010/0217353 A1 | 8/2010 | Forsell |
| 2010/0241195 A1 | 9/2010 | Meadows et al. |
| 2010/0319711 A1 | 12/2010 | Hegde et al. |
| 2011/0009920 A1 | 1/2011 | Whitehurst et al. |
| 2011/0071591 A1 | 3/2011 | Bolea et al. |
| 2011/0093048 A1 | 4/2011 | Aghassian |
| 2011/0112601 A1 | 5/2011 | Meadows et al. |
| 2011/0152706 A1 | 6/2011 | Christopherson et al. |
| 2011/0160794 A1 | 6/2011 | Bolea et al. |
| 2011/0172733 A1 | 7/2011 | Lima et al. |
| 2011/0202119 A1 | 8/2011 | Ni et al. |
| 2011/0213438 A1 | 9/2011 | Lima et al. |
| 2011/0218408 A1 | 9/2011 | Green et al. |
| 2011/0240037 A1 | 10/2011 | Hegde et al. |
| 2011/0245734 A1 | 10/2011 | Wagner et al. |
| 2011/0265322 A1 | 11/2011 | Greenberg et al. |
| 2011/0275927 A1 | 11/2011 | Wagner et al. |
| 2011/0278948 A1 | 11/2011 | Forsell |
| 2012/0022609 A1 | 1/2012 | Bolea et al. |
| 2012/0065701 A1 | 3/2012 | Cauller |
| 2012/0109020 A1 | 5/2012 | Wagner et al. |
| 2012/0123498 A1 | 5/2012 | Gross |
| 2012/0192874 A1 | 8/2012 | Bolea et al. |
| 2012/0227748 A1 | 9/2012 | Sanders |
| 2012/0283795 A1 | 11/2012 | Stancer et al. |
| 2012/0286582 A1 | 11/2012 | Kim et al. |
| 2012/0290055 A1 | 11/2012 | Boggs, II |
| 2012/0303080 A1 | 11/2012 | Ben-David et al. |
| 2012/0323294 A1 | 12/2012 | Laing et al. |
| 2013/0002423 A1 | 1/2013 | Robertson et al. |
| 2013/0023958 A1* | 1/2013 | Fell ..................... A61N 1/3787 607/61 |
| 2013/0110195 A1 | 5/2013 | Fletcher et al. |
| 2013/0116745 A1 | 5/2013 | Fletcher et al. |
| 2013/0116763 A1* | 5/2013 | Parker ................. A61N 1/3787 607/117 |
| 2013/0165996 A1 | 6/2013 | Meadows et al. |
| 2013/0197615 A1 | 8/2013 | Rundle et al. |
| 2013/0213404 A1 | 8/2013 | Leibitzki et al. |
| 2013/0218251 A1 | 8/2013 | Penner |
| 2013/0238044 A1 | 9/2013 | Penner |
| 2013/0238066 A1 | 9/2013 | Boggs, II et al. |
| 2013/0274842 A1 | 10/2013 | Gaunt et al. |
| 2013/0338452 A1 | 12/2013 | Robertson et al. |
| 2014/0012342 A1 | 1/2014 | Penner et al. |
| 2014/0046407 A1 | 2/2014 | Ben-Ezra et al. |
| 2014/0046416 A1* | 2/2014 | Bennett ............... A61N 1/0502 607/116 |
| 2014/0058495 A1 | 2/2014 | Sakai et al. |
| 2014/0121741 A1 | 5/2014 | Bennett et al. |
| 2014/0152246 A1 | 6/2014 | Forsell |
| 2014/0155959 A1 | 6/2014 | Forsell |
| 2014/0163661 A1 | 6/2014 | Ben-David et al. |
| 2014/0207220 A1 | 7/2014 | Boling et al. |
| 2014/0214135 A1 | 7/2014 | Ben-David et al. |
| 2014/0249361 A1 | 9/2014 | DiUbaldi et al. |
| 2014/0323839 A1 | 10/2014 | McCreery |
| 2014/0330340 A1 | 11/2014 | Bennett et al. |
| 2014/0330356 A1 | 11/2014 | Bennett et al. |
| 2014/0378740 A1 | 12/2014 | Wagner et al. |
| 2015/0025613 A1 | 1/2015 | Nyberg, II et al. |
| 2015/0039055 A1 | 2/2015 | Wagner et al. |
| 2015/0039067 A1 | 2/2015 | Greenberg et al. |
| 2015/0051678 A1 | 2/2015 | Reed et al. |
| 2015/0066106 A1 | 3/2015 | Greenberg et al. |
| 2015/0105702 A1 | 4/2015 | Wagner et al. |
| 2015/0105840 A1 | 4/2015 | Boggs, II |
| 2015/0119629 A1 | 4/2015 | Wagner et al. |
| 2015/0134037 A1 | 5/2015 | Bennett et al. |
| 2015/0142075 A1 | 5/2015 | Miller, III et al. |
| 2015/0142120 A1 | 5/2015 | Papay |
| 2015/0148713 A1 | 5/2015 | Wagner et al. |
| 2015/0151123 A1 | 6/2015 | Wagner et al. |
| 2015/0174409 A1 | 6/2015 | Parker et al. |
| 2015/0264816 A1 | 9/2015 | Askin, III et al. |
| 2015/0321004 A1 | 11/2015 | Reed et al. |
| 2015/0321008 A1 | 11/2015 | Tesfayesus et al. |
| 2015/0321018 A1 | 11/2015 | Fletcher et al. |
| 2015/0328455 A1 | 11/2015 | Meadows et al. |
| 2015/0374985 A1 | 12/2015 | Fahey |
| 2015/0374998 A1 | 12/2015 | Fletcher et al. |
| 2016/0001079 A1 | 1/2016 | Fletcher et al. |
| 2016/0008608 A1 | 1/2016 | Boling et al. |
| 2016/0022481 A1 | 1/2016 | Fahey et al. |
| 2016/0030746 A1 | 2/2016 | Reed et al. |
| 2016/0059011 A1 | 3/2016 | Bolea et al. |
| 2016/0067396 A1 | 3/2016 | Stark et al. |
| 2016/0089540 A1 | 3/2016 | Bolea |
| 2016/0114174 A1 | 4/2016 | Colvin et al. |
| 2016/0114175 A1 | 4/2016 | Colvin et al. |
| 2016/0114177 A1 | 4/2016 | Colvin et al. |
| 2016/0135746 A1 | 5/2016 | Kumar et al. |
| 2016/0144180 A1 | 5/2016 | Simon et al. |

FOREIGN PATENT DOCUMENTS

| | | |
|---|---|---|
| DE | 69529951 T2 | 2/2004 |
| DE | 69722782 T2 | 2/2004 |
| DE | 69629238 T2 | 5/2004 |
| DE | 69532514 T2 | 10/2004 |
| DE | 69730842 T2 | 9/2005 |
| DE | 69927438 T2 | 6/2006 |
| DE | 69928748 T2 | 6/2006 |
| DE | 69636883 T2 | 10/2007 |
| DE | 60315327 T2 | 1/2008 |
| DE | 69535686 T2 | 1/2009 |
| DE | 112008001669 T5 | 5/2010 |
| DE | 202007019439 U1 | 9/2012 |
| EP | 0702977 B1 | 3/1996 |

(56) References Cited

FOREIGN PATENT DOCUMENTS

| | | |
|---|---|---|
| EP | 0706808 B1 | 4/1996 |
| EP | 0743076 B1 | 11/1996 |
| EP | 0814868 B1 | 1/1998 |
| EP | 0970713 B1 | 1/2000 |
| EP | 0998328 B1 | 5/2000 |
| EP | 1052935 B1 | 11/2000 |
| EP | 1175919 B1 | 1/2002 |
| EP | 1277491 B1 | 1/2003 |
| EP | 1306104 B1 | 5/2003 |
| EP | 1331969 B1 | 8/2003 |
| EP | 1389079 B1 | 2/2004 |
| EP | 1429837 B1 | 6/2004 |
| EP | 1446188 B1 | 8/2004 |
| EP | 1494753 B1 | 1/2005 |
| EP | 1507473 B1 | 2/2005 |
| EP | 1524007 A1 | 4/2005 |
| EP | 1545693 B1 | 6/2005 |
| EP | 1554012 B1 | 7/2005 |
| EP | 1608432 B1 | 12/2005 |
| EP | 1609502 A1 | 12/2005 |
| EP | 1613396 B1 | 1/2006 |
| EP | 1648559 B1 | 4/2006 |
| EP | 1675648 B1 | 7/2006 |
| EP | 1676526 B1 | 7/2006 |
| EP | 1682222 B1 | 7/2006 |
| EP | 1706178 B1 | 10/2006 |
| EP | 1750801 B1 | 2/2007 |
| EP | 1776922 A1 | 4/2007 |
| EP | 1861162 B1 | 12/2007 |
| EP | 1874397 A2 | 1/2008 |
| EP | 1897586 B1 | 3/2008 |
| EP | 1904153 B1 | 4/2008 |
| EP | 1907048 A2 | 4/2008 |
| EP | 1981583 B1 | 10/2008 |
| EP | 1981589 B1 | 10/2008 |
| EP | 2036588 B1 | 3/2009 |
| EP | 2040790 B1 | 4/2009 |
| EP | 2089100 B1 | 8/2009 |
| EP | 2116274 B1 | 11/2009 |
| EP | 2143465 B1 | 1/2010 |
| EP | 2167187 A2 | 3/2010 |
| EP | 2228095 A3 | 9/2010 |
| EP | 2243509 A1 | 10/2010 |
| EP | 2266164 B1 | 12/2010 |
| EP | 2272562 A1 | 1/2011 |
| EP | 2286871 B1 | 2/2011 |
| EP | 2289596 B1 | 3/2011 |
| EP | 2298408 A2 | 3/2011 |
| EP | 2310088 B1 | 4/2011 |
| EP | 2318088 B1 | 5/2011 |
| EP | 2380625 A1 | 10/2011 |
| EP | 2383015 A1 | 11/2011 |
| EP | 2462982 A1 | 6/2012 |
| EP | 2468358 B1 | 6/2012 |
| EP | 2476458 B1 | 7/2012 |
| EP | 2478931 B1 | 7/2012 |
| EP | 2550992 B1 | 1/2013 |
| EP | 2462983 A1 | 6/2013 |
| EP | 2617396 A2 | 7/2013 |
| EP | 2617457 A2 | 7/2013 |
| EP | 2617460 A2 | 7/2013 |
| EP | 2667933 B1 | 12/2013 |
| EP | 2905051 A1 | 8/2015 |
| EP | 2907542 A1 | 8/2015 |
| EP | 2932998 A1 | 10/2015 |
| EP | 2965782 A1 | 1/2016 |
| EP | 3002035 A1 | 4/2016 |
| EP | 2211977 A1 | 6/2016 |
| JP | 06-007724 Y | 3/1994 |
| JP | 11-195921 A | 7/1999 |
| JP | 2007-13662 | 1/2007 |
| JP | 2011-500143 A | 1/2011 |
| JP | 4953996 B | 3/2012 |
| WO | WO 96/40367 | 12/1996 |
| WO | WO 97/37720 | 10/1997 |
| WO | WO 97/49454 | 12/1997 |
| WO | WO 98/11942 | 3/1998 |
| WO | WO 98/24510 | 6/1998 |
| WO | WO 99/39769 | 8/1999 |
| WO | WO 99/62594 | 12/1999 |
| WO | WO 00/02212 | 1/2000 |
| WO | WO 00/24456 | 5/2000 |
| WO | WO 01/39830 | 6/2001 |
| WO | WO 01/78216 | 10/2001 |
| WO | WO 03/009749 | 2/2003 |
| WO | WO 03/061335 | 7/2003 |
| WO | WO 03/066153 | 8/2003 |
| WO | WO 03/099377 | 12/2003 |
| WO | WO 2004/002572 | 1/2004 |
| WO | WO 2004/008954 | 1/2004 |
| WO | WO 2004/028624 | 4/2004 |
| WO | WO 2004/064729 | 8/2004 |
| WO | WO 2004/103455 | 12/2004 |
| WO | WO 2004/110549 | 12/2004 |
| WO | WO 2004/110550 | 12/2004 |
| WO | WO 2005/011805 | 2/2005 |
| WO | WO 2005/037370 | 4/2005 |
| WO | WO 2005/077276 | 8/2005 |
| WO | WO 2005/082452 | 9/2005 |
| WO | WO 2006/093964 | 9/2006 |
| WO | WO 2006/132810 | 12/2006 |
| WO | WO 2007/035361 | 3/2007 |
| WO | WO 2007/035774 | 3/2007 |
| WO | WO 2007/081714 | 7/2007 |
| WO | WO 2007/090047 | 8/2007 |
| WO | WO 2007/092865 | 8/2007 |
| WO | WO 2007/098202 | 8/2007 |
| WO | WO 2007/120305 | 10/2007 |
| WO | WO 2007/149571 | 12/2007 |
| WO | WO 2008/005903 | 1/2008 |
| WO | WO 2008/014028 | 1/2008 |
| WO | WO 2008/016802 | 2/2008 |
| WO | WO 2008/039921 | 4/2008 |
| WO | WO 2008/042058 | 4/2008 |
| WO | WO 2008/048724 | 4/2008 |
| WO | WO 2008/079700 | 7/2008 |
| WO | WO 2008/076646 | 8/2008 |
| WO | WO 2009/032625 | 3/2009 |
| WO | WO 2009/046044 | 4/2009 |
| WO | WO 2009/048580 | 4/2009 |
| WO | WO 2009/051536 | 4/2009 |
| WO | WO 2009/051538 | 4/2009 |
| WO | WO 2009/051539 | 4/2009 |
| WO | WO 2009/061537 | 5/2009 |
| WO | WO 2009/070086 | 6/2009 |
| WO | WO 2009/111012 | 9/2009 |
| WO | WO 2009/126354 | 10/2009 |
| WO | WO 2009/140636 | 11/2009 |
| WO | WO 2010/003106 | 1/2010 |
| WO | WO 2010/039853 | 4/2010 |
| WO | WO 2010/042020 | 4/2010 |
| WO | WO 2010/042404 | 4/2010 |
| WO | WO 2010/096776 | 8/2010 |
| WO | WO 2011/060056 | 5/2011 |
| WO | WO 2011/139779 | 11/2011 |
| WO | WO 2011/143490 | 11/2011 |
| WO | WO 2012/030522 | 3/2012 |
| WO | WO 2012/055389 | 5/2012 |
| WO | WO 2013/067538 | 5/2013 |
| WO | WO 2013/078092 | 5/2013 |
| WO | WO 2013/086212 | 6/2013 |
| WO | WO 2013/147799 | 10/2013 |
| WO | WO 2013/173214 | 11/2013 |
| WO | WO 2013/188400 | 12/2013 |
| WO | WO 2014/004526 | 1/2014 |
| WO | WO 2014/0179685 | 11/2014 |

OTHER PUBLICATIONS

International Search Report and Written Opinion for PCT/IB13/02101, dated Feb. 10, 2014 (8 pages).

* cited by examiner

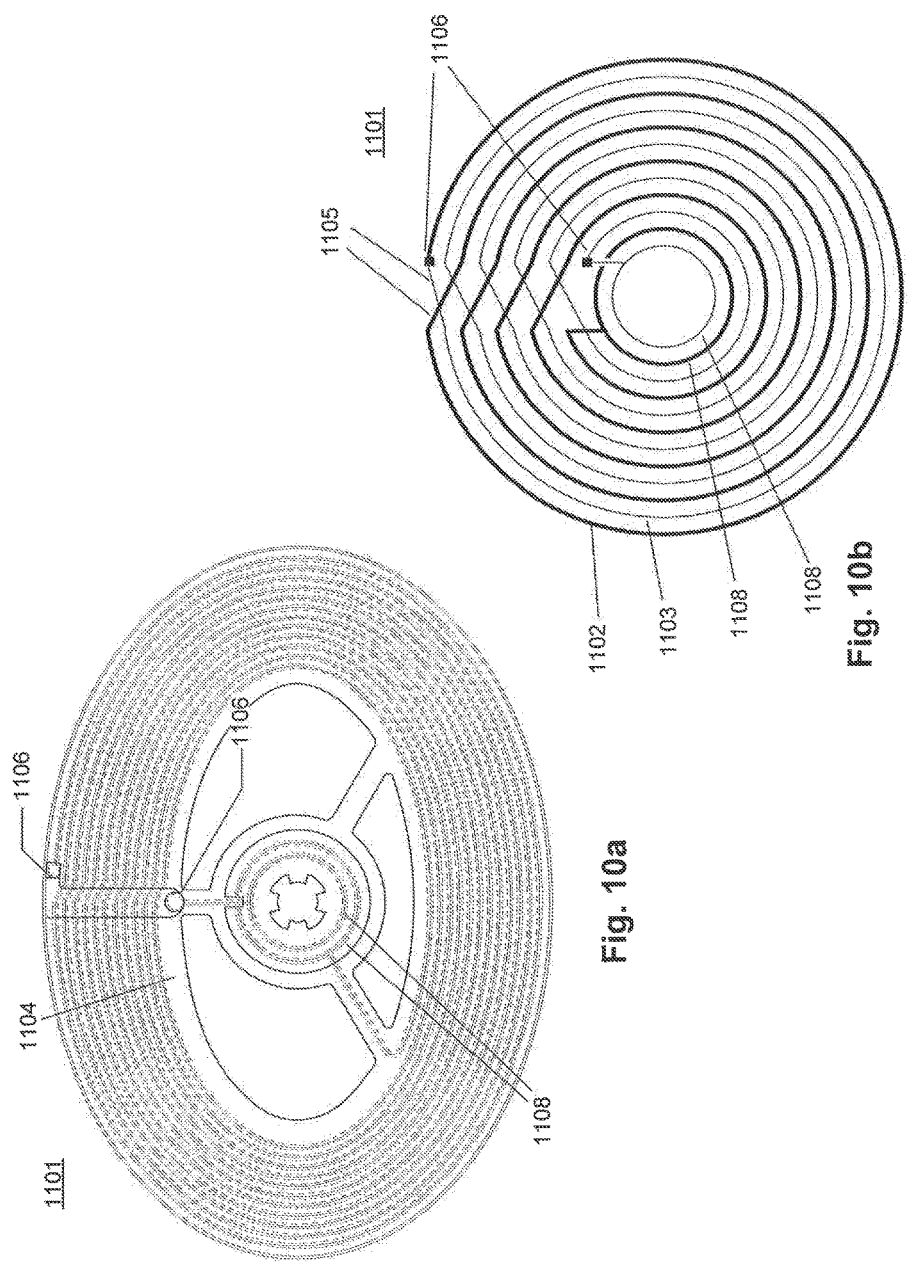

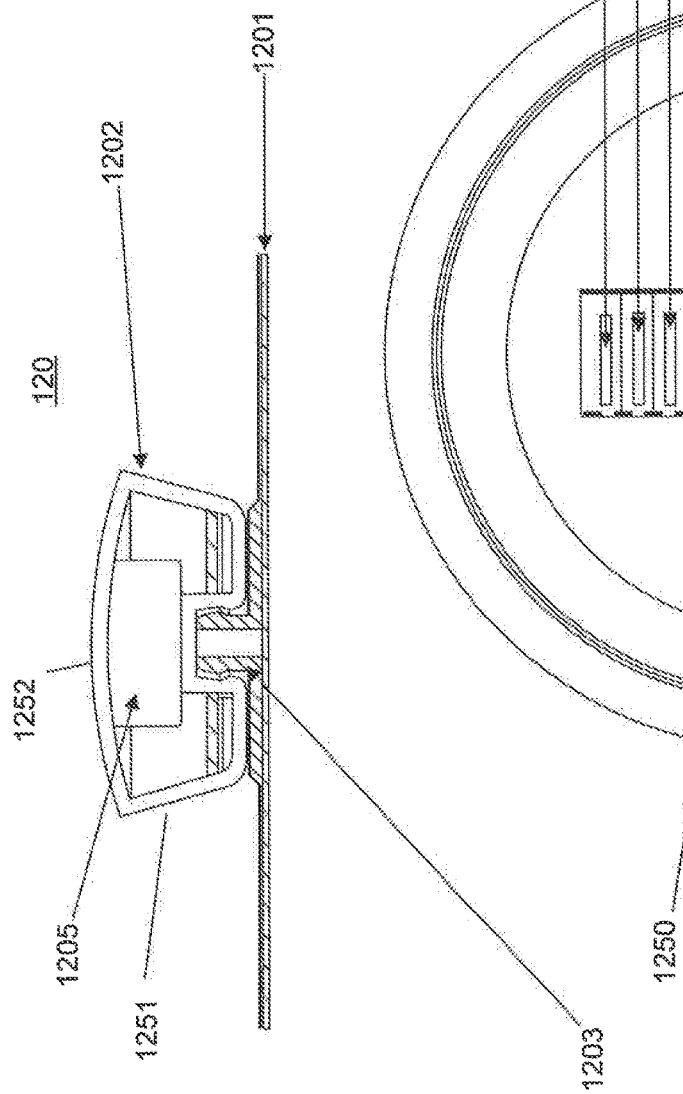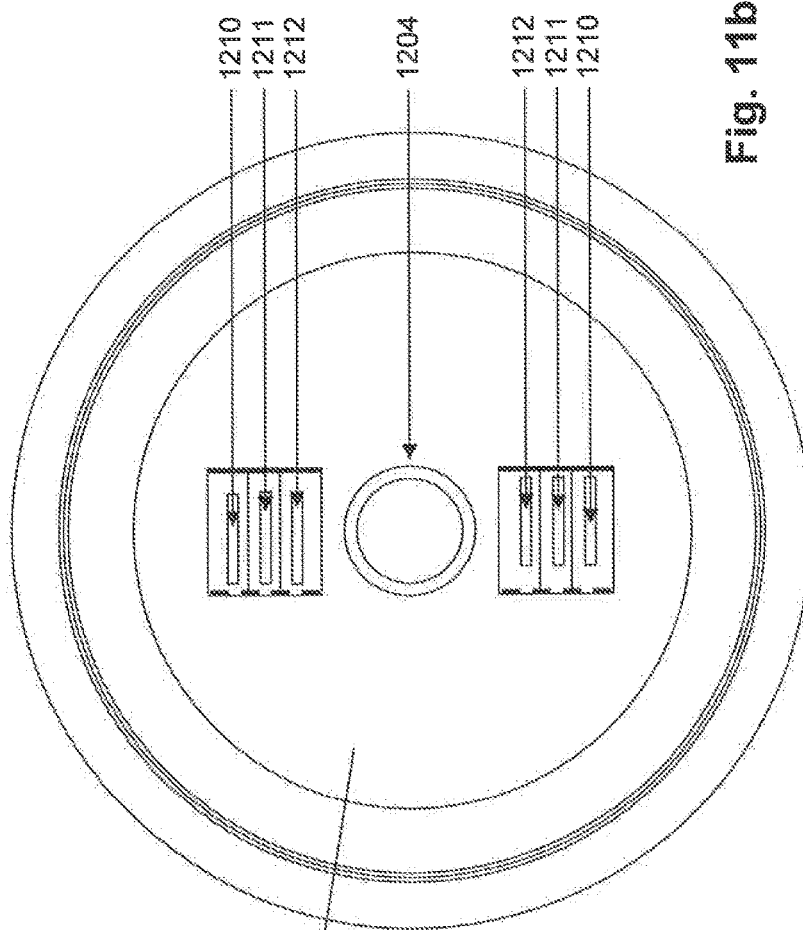

THERAPY PROTOCOL ACTIVATION TRIGGERED BASED ON INITIAL COUPLING

RELATED APPLICATIONS

This application claims the benefit of priority under 35 U.S.C. § 119(e) to U.S. Provisional Application No. 61/676,327, filed Jul. 26, 2012, which is incorporated herein by reference.

TECHNICAL FIELD

Embodiments of the present disclosure generally relate to devices and methods for modulating a nerve. More particularly, embodiments of the present disclosure relate to devices and methods for modulating a nerve through the delivery of energy via an implantable electrical modulator.

BACKGROUND

Neural modulation presents the opportunity to treat many physiological conditions and disorders by interacting with the body's own natural neural processes. Neural modulation includes inhibition (e.g. blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure. Neural modulation may provide the opportunity to treat several diseases or physiological conditions, a few examples of which are described in detail below.

Among the conditions to which neural modulation may be applied is obstructive sleep apnea (OSA). OSA is a respiratory disorder characterized by recurrent episodes of partial or complete obstruction of the upper airway during sleep. During the sleep of a person without OSA, the pharyngeal muscles relax during sleep and gradually collapse, narrowing the airway. The airway narrowing limits the effectiveness of the sleeper's breathing, causing a rise in $CO_2$ levels in the blood. The increase in $CO_2$ results in the pharyngeal muscles contracting to open the airway to restore proper breathing. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In patients with OSA, the neuromuscular activity of the genioglossus muscle is decreased compared to normal individuals, accounting for insufficient response and contraction to open the airway as compared to a normal individual. This lack of response contributes to a partial or total airway obstruction, which significantly limits the effectiveness of the sleeper's breathing. In OSA patients, there are often several airway obstruction events during the night. Because of the obstruction, there is a gradual decrease of oxygen levels in the blood (hypoxemia). Hypoxemia leads to night time arousals, which may be registered by EEG, showing that the brain awakes from any stage of sleep to a short arousal. During the arousal, there is a conscious breath or gasp, which resolves the airway obstruction. An increase in sympathetic tone activity rate through the release of hormones such as epinephrine and noradrenaline also often occurs as a response to hypoxemia. As a result of the increase in sympathetic tone, the heart enlarges in an attempt to pump more blood and increase the blood pressure and heart rate, further arousing the patient. After the resolution of the apnea event, as the patient returns to sleep, the airway collapses again, leading to further arousals.

These repeated arousals, combined with repeated hypoxemia, leaves the patient sleep deprived, which leads to daytime somnolence and worsens cognitive function. This cycle can repeat itself up to hundreds of times per night in severe patients. Thus, the repeated fluctuations in and sympathetic tone and episodes of elevated blood pressure during the night evolve to high blood pressure through the entire day. Subsequently, high blood pressure and increased heart rate may cause other diseases.

Efforts for treating OSA include Continuous Positive Airway Pressure (CPAP) treatment, which requires the patient to wear a mask through which air is blown into the nostrils to keep the airway open. Other treatment options include the implantation of rigid inserts in the soft palate to provide structural support, tracheotomies, or tissue ablation.

Another condition to which neural modulation may be applied is the occurrence of migraine headaches. Pain sensation in the head is transmitted to the brain via the occipital nerve, specifically the greater occipital nerve, and the trigeminal nerve. When a subject experiences head pain, such as during a migraine headache, the inhibition of these nerves may serve to decrease or eliminate the sensation of pain.

Neural modulation may also be applied to hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g. through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

The foregoing are just a few examples of conditions to which neuromodulation may be of benefit, however embodiments of the invention described hereafter are not necessarily limited to treating only the above-described conditions.

SUMMARY

One aspect of the present disclosure is directed to a control unit for cooperating with an adhesive patch to convey power from a location external to a subject to a location within the subject. The control unit may include a housing configured for selective mounting on the adhesive patch. The control unit may further include at least one processor within the housing. The at least one processor may be configured to activate when the housing is mounted on the adhesive patch. The at least one processor may be further configured to delay, for a predetermined amount of time following activation of the at least one processor, generation of therapeutic control signals for modulating at least one nerve in the subject's body.

Another aspect of the present disclosure is directed to a device for treatment of sleep disordered breathing. The device may include a patch configured for temporary affixation on a region including at least one of an underside of a chin, a neck, and a head of a subject. The device may further include a control unit. The control unit may include a housing configured for selective mounting on the patch, and at least one processor. The at least one processor may be configured to activate when the housing is mounted on the patch. The at least one processor may be further configured to delay, for a predetermined amount of time following activation of the at least one processor, generation of therapeutic control signals for modulation of at least one nerve of the subject's body.

Yet another aspect of the present disclosure is direct to a method of activating a therapy protocol for delivery of power to an implant. The method may include engaging a control unit with an adhesive patch. The control unit may include a housing and at least one processor within the housing. The method may further include activating the at least one processor when the housing is mounted on the adhesive patch, and enabling the at least one processor to generate therapeutic control signals for modulating at least one nerve in the subject's body. The method may also include delaying, for a predetermined amount of time following activation of the at least one processor, generation of therapeutic control signals by the at least one processor.

Additional features of the disclosure will be set forth in part in the description that follows, and in part will be obvious from the description, or may be learned by practice of the disclosed embodiments.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIGS. 10a and 10b illustrate a double-layer crossover antenna, according to exemplary embodiments of the present disclosure.

FIGS. 11a and 11b illustrate components of the external unit, according to exemplary embodiments of the present disclosure.

DESCRIPTION OF EXEMPLARY EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to a device for modulating a nerve through the delivery of energy. Nerve modulation, or neural modulation, includes inhibition (e.g. blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may include providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied.

In patients with OSA, for example, a primary target response of nerve stimulation may include contraction of a tongue muscle (e.g., the muscle) in order to move the tongue to a position that does not block the patient's airway. In the treatment of migraine headaches, nerve inhibition may be used to reduce or eliminate the sensation of pain. In the treatment of hypertension, neural modulation may be used to increase, decrease, eliminate or otherwise modify nerve signals generated by the body to regulate blood pressure.

While embodiments of the present disclosure may be disclosed for use in patients with specific conditions, the embodiments may be used in conjunction with any patient/portion of a body where nerve modulation may be desired. That is, in addition to use in patients with OSA, migraine headaches, or hypertension, embodiments of the present disclosure may be use in many other areas, including, but not limited to: deep brain stimulation (e.g., treatment of epilepsy, Parkinson's, and depression); cardiac pace-making, stomach muscle stimulation (e.g., treatment of obesity), back pain, incontinence, menstrual pain, and/or any other condition that may be affected by neural modulation.

Figure 1:
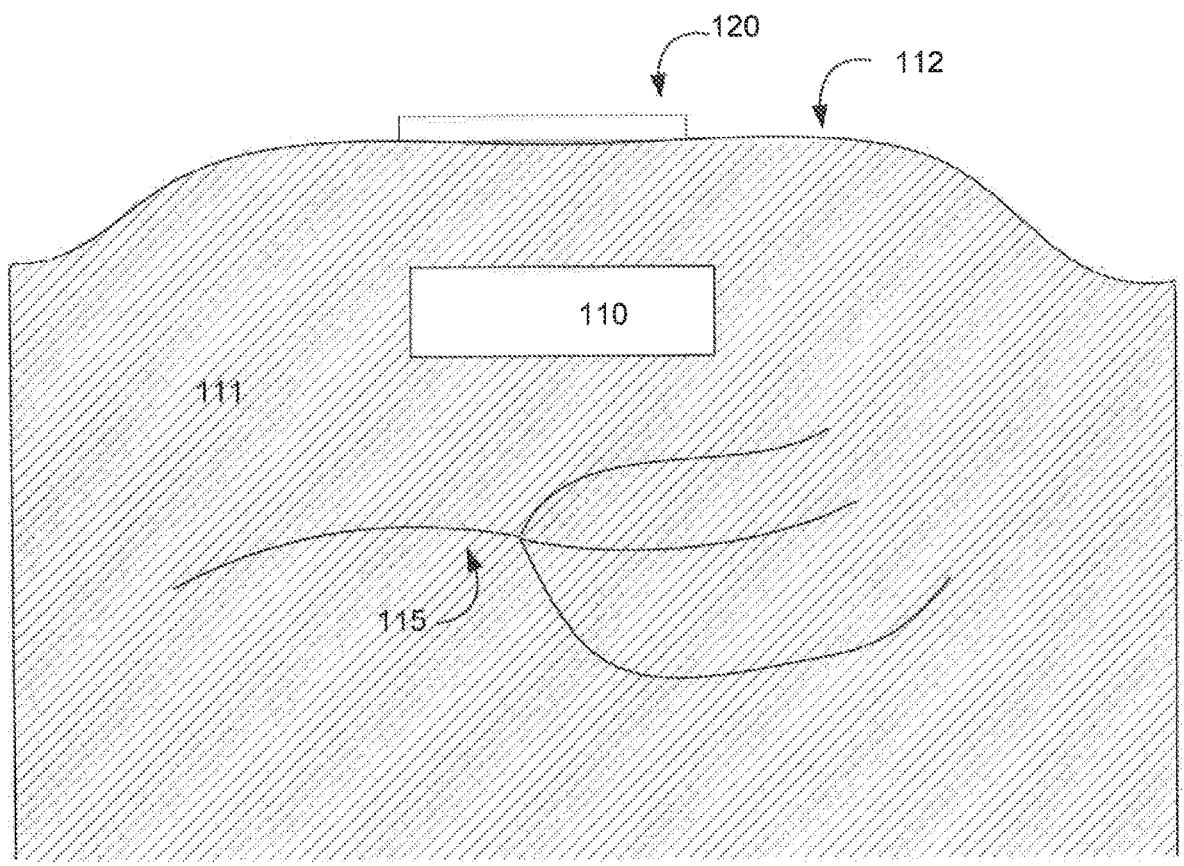
FIG. 1 diagrammatically illustrates an implant unit and external unit, according to an exemplary embodiment of the present disclosure.

FIG. 1 illustrates an implant unit and an external unit, according to an exemplary embodiment of the present disclosure. Implant unit 110 may be configured for implantation in a subject, in a location that permits it to modulate a nerve 115. For example, implant unit 110 may be located in a subject such that intervening tissue 111 exists between implant unit 110 and nerve 115. Intervening tissue may include muscle tissue, connective tissue, organ tissue, or any other type of biological tissue. Thus, location of implant unit 110 does not require contact with nerve 115 for effective neuromodulation. Implant unit 110 may also be located directly adjacent to nerve 115, such that no intervening tissue 111 exists.

In treating OSA, implant unit 110 may be located on a genioglossus muscle of a patient. Such a location is suitable for modulation of the hypoglossal nerve, branches of which run inside the genioglossus muscle. Implant unit 110 may also be configured for placement in other locations. For example, migraine treatment may require subcutaneous implantation in the back of the neck, near the hairline of a subject, or behind the ear of a subject, to modulate the greater occipital nerve and/or the trigeminal nerve. Treating hypertension may require the implantation of a neuromodulation implant intravascularly inside the renal artery or renal vein (to modulate the parasympathetic renal nerves, either unilaterally or bilaterally, inside the carotid artery or jugular vein (to modulate the glossopharyngeal nerve through the carotid baroreceptors). Alternatively or additionally, treating hypertension may require the implantation of a neuromodulation implant subcutaneously, behind the ear or in the neck, for example, to directly modulate the glossopharyngeal nerve.

External unit 120 may be configured for location external to a patient, either directly contacting, or close to the skin 112 of the patient. External unit 120 may be configured to be affixed to the patient, for example, by adhering to the skin 112 of the patient, or through a band or other device configured to hold external unit 120 in place. Adherence to the skin of external unit 120 may occur such that it is in the vicinity of the location of implant unit 110.

Figure 2:
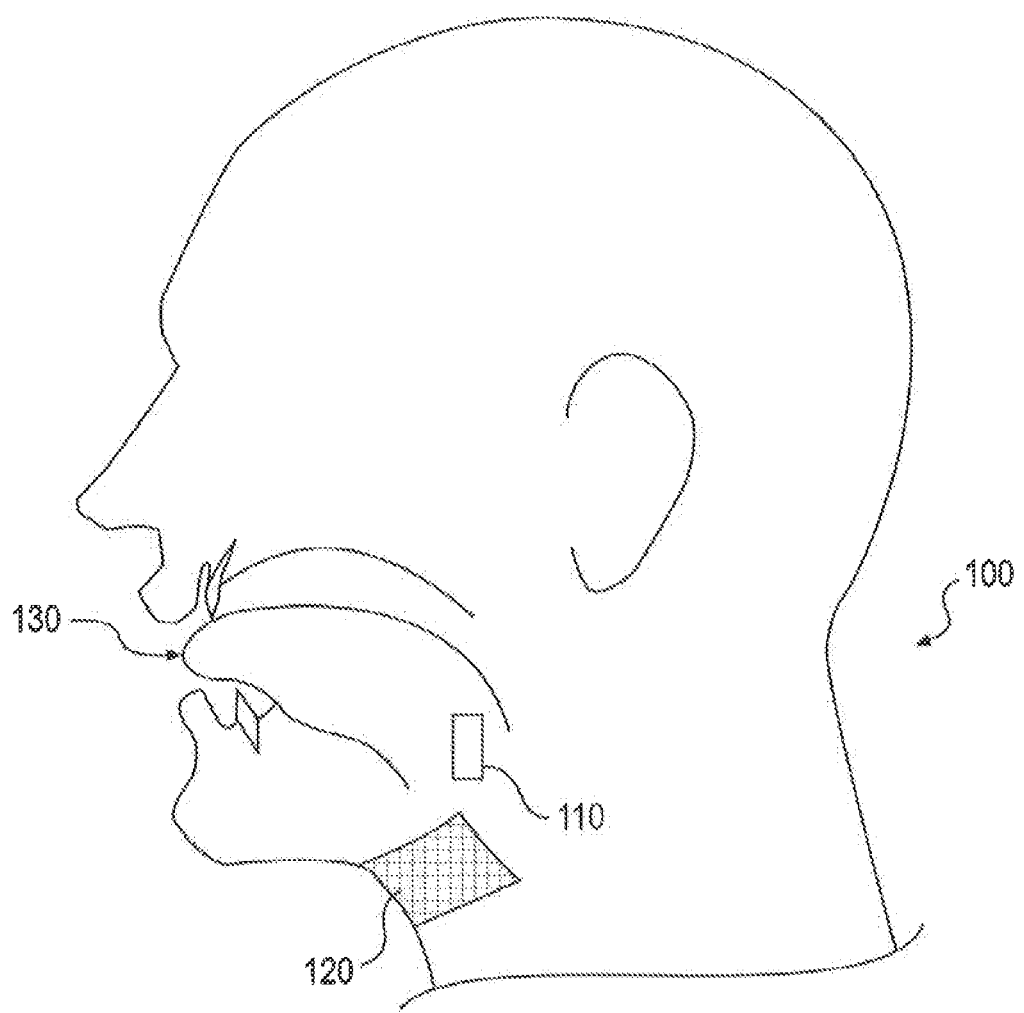
FIG. 2 is a partially cross-sectioned side view of a subject with an implant unit and external unit, according to an exemplary embodiment of the present disclosure.

FIG. 2 illustrates an exemplary embodiment of a neuromodulation system for delivering energy in a patient 100 with OSA. The system may include an external unit 120 that may be configured for location external to the patient. As illustrated in FIG. 2, external unit 120 may be configured to be affixed to the patient 100. FIG. 2 illustrates that in a patient 100 with OSA, external unit 120 may be configured for placement underneath the patient's chin and/or on the front of patient's neck. The suitability of placement locations may be determined by communication between external unit 120 and implant unit 110, which is discussed in greater detail below. In alternate embodiments, for the treatment of conditions other than OSA, the external unit may be configured to be affixed to any other suitable location on a patient, such as the back of a patient's neck, i.e., for communication with a migraine treatment implant unit, on the outer portion of a patient's abdomen, i.e., for communication with a stomach modulating implant unit, on a patient's back, i.e., for communication with a renal artery modulating implant unit, and/or on any other suitable external location on a patient's skin, depending on the requirements of a particular application.

External unit 120 may further be configured to be affixed to an alternative location proximate to the patient. For example, in one embodiment, the external unit may be configured to fixedly or removably adhere to a strap or a band that may be configured to wrap around a part of a patient's body. Alternatively, or in addition, the external unit may be configured to remain in a desired location external to the patient's body without adhering to that location.

External unit 120 may be comprised of multiple components. An exemplary embodiment of external unit 120 is discussed below with reference to FIGS. 11a and 11b. More generally, external unit 120 may include a housing. The housing may include any suitable container configured for retaining components. In addition, while the external unit is illustrated schematically in FIG. 2, the housing may include any suitable size and/or shape and may be rigid or flexible. Non-limiting examples of housings for the external unit 120 include one or more of patches, buttons, or other receptacles having varying shapes and dimensions and constructed of any suitable material. In one embodiment, for example, the housing may include a flexible material such that the external unit may be configured to conform to a desired location. For example, as illustrated in FIG. 2, external unit 120 may include a skin patch, which, in turn, may include a flexible substrate. The material of the flexible substrate may include, but is not limited to, plastic, silicone, woven natural fibers, and other suitable polymers, copolymers, and combinations thereof. Any portion of external unit 120 may be flexible or rigid, depending on the requirements of a particular application.

As previously discussed, in some embodiments external unit 120 may be configured to adhere to a desired location. Accordingly, in some embodiments, at least one side of the housing may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions.

Figure 3:
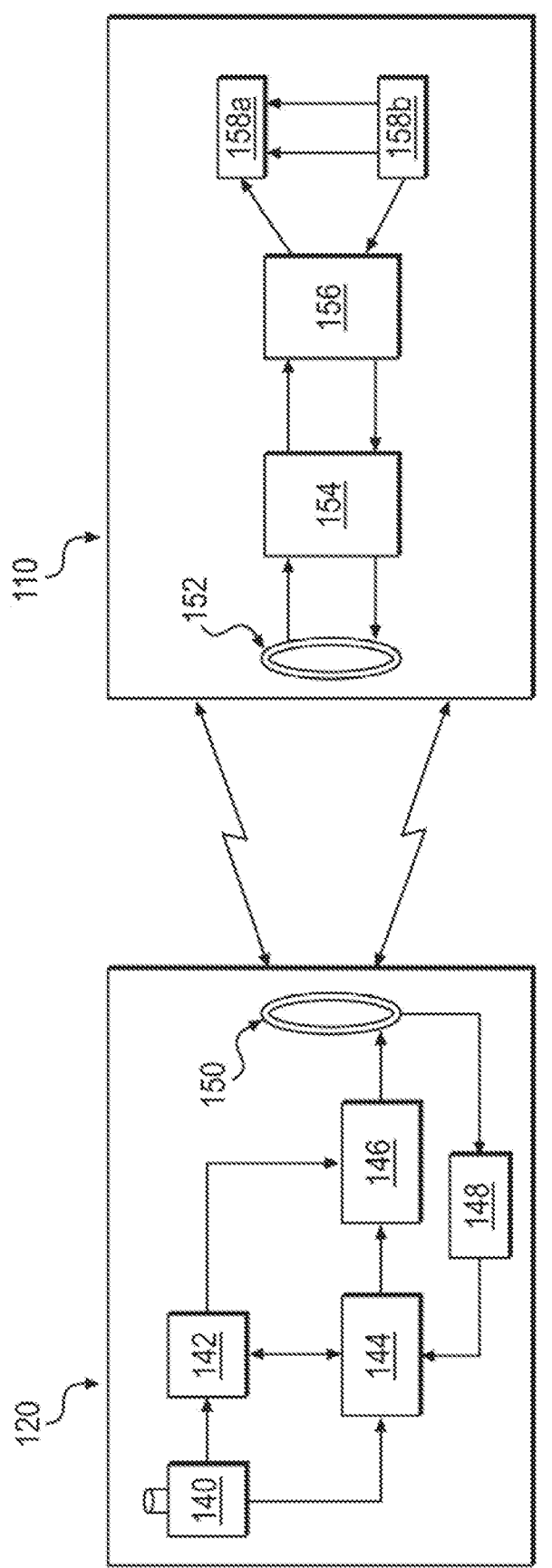
FIG. 3 diagrammatically illustrates a system including an implant unit and an external unit, according to an exemplary embodiment of the present disclosure.

FIG. 3 schematically illustrates a system including external unit 120 and an implant unit 110. In some embodiments, internal unit 110 may be configured as a unit to be implanted into the body of a patient, and external unit 120 may be configured to send signals to and/or receive signals from implant unit 110.

As shown in FIG. 3, various components may be included within a housing of external unit 120 or otherwise associated with external unit 120. As illustrated in FIG. 3, at least one processor 144 may be associated with external unit 120. For example, the at least one processor 144 may be located within the housing of external unit 120. In alternative embodiments, the at least one processor may be configured for wired or wireless communication with the external unit from a location external to the housing.

The at least one processor 144 may include any electric circuit that may be configured to perform a logic operation on at least one input variable. The at least one processor may therefore include one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

FIG. 3 illustrates that external unit 120 may further be associated with a power source 140. The power source may be removably couplable to the external unit at an exterior location relative to external unit. Alternatively, as shown in FIG. 3, power source 140 may be permanently or removably coupled to a location within external unit 120. The power source may further include any suitable source of power configured to be in electrical communication with the at least one processor 144. In one embodiment, for example power source 140 may include a battery.

Power source 140 may be configured to power various components within external unit 120. As illustrated in FIG. 3, power source 140 may be configured to provide power to the at least one processor 144. In addition, power source 140 may be configured to provide power to a signal source 142. Signal source 142 may be in communication with the at least one processor 144 and may include any device configured to generate a signal (e.g., a sinusoidal signal, square wave, triangle wave, microwave, radio-frequency (RF) signal, or any other type of electromagnetic signal). Signal source 142 may include, but is not limited to, a waveform generator that may be configured to generate alternating current (AC) signals and/or direct current (DC) signals. In one embodiment, for example, signal source 142 may be configured to generate an AC signal for transmission to one or more other components. Signal source 142 may be configured to generate a signal of any suitable frequency. In some embodiments, signal source 142 may be configured to generate a signal having a frequency of from about 6.5 MHz to about 13.6 MHz. In additional embodiments, signal source 142 may be configured to generate a signal having a frequency of from about 7.4 to about 8.8 MHz. In further embodiments, signal source 142 may generate a signal having a frequency as low as 90 kHz or as high as 28 MHz.

Signal source 142 may be configured for direct or indirect electrical communication with an amplifier 146. Amplifier 146 may include any suitable device configured to amplify one or more signals generated from signal source 142. Amplifier 146 may include one or more of various types of amplification devices, including, for example, transistor based devices, operational amplifiers, RF amplifiers, power amplifiers, or any other type of device that can increase the gain associated one or more aspects of a signal. Amplifier 146 may further be configured to output the amplified signals to one or more components within external unit 120.

External unit 120 may additionally include a primary antenna 150. The primary antenna may be configured as part of a circuit within external unit 120, and may be coupled either directly or indirectly to various components in external unit 120. For example, as shown in FIG. 3, primary antenna 150 may be configured for communication with amplifier 146.

Primary antenna 150 may include any conductive structure that may be configured to create an electromagnetic field. Primary antenna 150 may further be of any suitable size, shape, and/or configuration. The size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. Primary antenna 150 may include any suitable antenna known to those skilled in the art that may be configured to send and/or receive signals. Suitable antennas may include, but are not limited to, a long-wire antenna, a patch antenna, a helical antenna, etc. In one embodiment, for example, as illustrated in FIG. 3, primary antenna 150 may include a coil antenna. Such a coil antenna may be made from any suitable conductive material and may be configured to include any suitable arrangement of conductive coils (e.g., diameter, number of coils, layout of coils, etc.). A coil antenna suitable for use as primary antenna 150 may have a diameter of between about 1 cm and 10 cm, and may be circular or oval shaped. In some embodiments, a coil antenna may have a diameter between 5 cm and 7 cm, and may be oval shaped. A coil antenna suitable for use as primary antenna 150 may have any number of windings, e.g. 4, 8, 12, or more. A coil antenna suitable for use as primary antenna 150 may have a wire diameter between about 0.01 mm and 2 mm. These antenna parameters are exemplary only, and may be adjusted above or below the ranges given to achieve suitable results.

As noted above, implant unit 110 may be configured to be implanted in a patient's body (e.g., beneath the patient's skin). FIG. 2 illustrates that the implant unit 110 may be configured to be implanted for modulation of a nerve associated with a muscle of the subject's tongue 130. Modulating a nerve associated with a muscle of the subject's tongue 130 may include stimulation to cause a muscle contraction. In further embodiments, the implant unit may be configured to be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e. the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

Implant unit 110 may be formed of any materials suitable for implantation into the body of a patient. In some embodiments, implant unit 110 may include a flexible carrier 161 (FIG. 4) including a flexible, biocompatible material. Such materials may include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a thickness suitable for implantation under a patient's skin. Implant 110 may have thickness of less than about 4 mm or less than about 2 mm.

Other components that may be included in or otherwise associated with the implant unit are illustrated in FIG. 3. For example, implant unit 110 may include a secondary antenna 152 mounted onto or integrated with flexible carrier 161. Similar to the primary antenna, secondary antenna 152 may include any suitable antenna known to those skilled in the art that may be configured to send and/or receive signals. Secondary antenna 152 may include any suitable size, shape, and/or configuration. The size, shape and/or configuration may be determined by the size of the patient, the placement location of implant unit 110, the amount of energy required to modulate the nerve, etc. Suitable antennas may include, but are not limited to, a long-wire antenna, a patch antenna, a helical antenna, etc. In some embodiments, for example, secondary antenna 152 may include a coil antenna having a circular shape (see also FIG. 4) or oval shape. Such a coil antenna may be made from any suitable conductive material and may be configured to include any suitable arrangement of conductive coils (e.g., diameter, number of coils, layout of coils, etc.). A coil antenna suitable for use as secondary antenna 152 may have a diameter of between about 5 mm and 30 mm, and may be circular or oval shaped. A coil antenna suitable for use as secondary antenna 152 may have any number of windings, e.g. 4, 15, 20, 30, or 50. A coil antenna suitable for use as secondary antenna 152 may have a wire diameter between about 0.001 mm and 1 mm. These antenna parameters are exemplary only, and may be adjusted above or below the ranges given to achieve suitable results.

FIGS. 10a and 10b illustrate a double-layer crossover antenna 1101 suitable for use as either primary antenna 150 or secondary antenna 152. While a double-layer crossover antenna is shown and described, other antenna configurations may be suitable for primary antenna 150 and/or secondary antenna 152. For example, single layer antennas may be used where antenna components (e.g., coils) are arranged in a single layer, e.g., either on or within a dielectric or insulating material. Also, while a crossover pattern is shown, other patterns may also be suitable. For example, in some embodiments, a wire associated with primary antenna 150 and/or secondary antenna 152 may include a pattern of traces of progressively decreasing dimension. In the case of traces arranged in coils, for example, each loop could include rings of progressively decreasing diameter to create a pattern that spirals inwardly. A similar approach may be viable using traces of other shapes as well.

Returning to FIG. 10a, this figure illustrates a single coil of double-layer crossover antenna 1101, while FIG. 10b illustrates two layers of double layer crossover antenna 1101. Antenna 1101 may include a first coil of wire 1102 arranged on a first side of a dielectric carrier 1104 and a second coil of wire 1103 on a second side of a dielectric carrier 1104.

Arranging the antenna coils in a double layer may serve to increase the transmission range of the antenna without increasing the size of the antenna. Such an arrangement, however, may also serve to increase capacitance between the wires of each coil. In each wire coil, an amount of parasitic capacitance between wires may partially depend on the distance each wire is from its neighbor. In a single layer coil, capacitance may be generated between each loop of the coil and its neighbors to either side. Thus, more compact coils may generate more parasitic capacitance. When a second layer coil is added, additional capacitance may then be generated between the wires of the first coil and the wires of the second coil. This additional capacitance may be further increased if corresponding loops of the first and second coils have the same or similar diameters, and/or if a dielectric carrier separating the loops is made very thin. Increased parasitic capacitance in an antenna may serve to alter characteristics, such as resonant frequency, of the antenna in unpredictable amounts based on manufacturing specifications. Additionally, resonant frequency drift, caused, for example by moisture incursion or antenna flexing, may be increased by the presence of increased parasitic capacitance. Thus, in order to decrease variability in the manufactured product, it may be advantageous to reduce the levels of parasitic capacitance in a dual layer antenna.

The double layer crossover antenna 1101 of FIG. 10b may serve to reduce the parasitic capacitance in a manufactured antenna. As illustrated in FIG. 10b, a first coil of wire 1102 is concentrically offset from a second coil of wire 1103. In contrast to a configuration where each loop of a first coil 1102 has the same diameter as corresponding loop of the second coil 1103, concentrically offsetting corresponding loops of each wire coil serves to increase the distance between a single loop of the first coil 1102 with a corresponding loop of the second coil 1103. This increased distance, in turn, may decrease the parasitic wire-to-wire capacitance between loops of first coil 1102 and corresponding loops of second coil 1103. This configuration may be particularly advantageous in reducing parasitic capacitance in a situation where a dielectric carrier 1104 is thin enough such that the concentric distance by which each coil is offset is relatively large compared to the thickness of the dielectric carrier 1104. For example, in a situation where a dielectric carrier is 0.5 mm thick, a concentric offset of 0.5 mm or more may produce a large change in parasitic capacitance. In contrast, in a situation where a dielectric carrier is 5 mm thick, a concentric offset of 0.5 mm may produce a smaller change in parasitic capacitance. The concentric offset between a first coil 1102 and a second coil 1103 may be achieved, for example, by a plurality of electrical trace steps 1105 that offset each loop of the coils from each preceding loop. Electrical trace steps 1105 on a first side of dielectric carrier 1104 cross over electrical trace steps 1105 on a second side of dielectric carrier 1104, thus providing the crossover feature of double-layer crossover antenna 1101.

In additional embodiments, double layer crossover antenna 1101 may include openings 1106 in dielectric carrier 1104 to facilitate the electrical connection of first and second coils 1102, 1103. First and second coils 1102, 1103 of double layer crossover antenna 1101 may also include exposed electrical portions 1108 configured to electrically connect with a connector of a housing that may be coupled to antenna 1101. Exposed electrical portions 1108 may be configured so as to maintain electrical contact with the connector of a housing independent of the axial orientation of the connection. As shown in FIG. 10a, for example, exposed electrical portions 1108 may be configured as continuous or discontinuous circles in order to achieve this. A first exposed electrical portion 1108 configured as a discontinuous circle may provide a space through which an electrical trace may pass without contacting the first exposed electrical portion, for example to connect with a second exposed electrical portion located inside the first, or to other components located within the circle of the first exposed electrical portion 1108. FIG. 10a illustrates an antenna having substantially elliptical coils; other shapes, such as circular, triangular, square, etc., may be also be used in different embodiments. Elliptical coils may facilitate placement of external unit 120 in certain areas (e.g., under the chin of a subject) while maintaining desirable electrical performance characteristics.

FIGS. 11a and 11b illustrate an exemplary embodiment of external unit 120. As shown in these figures, external unit 120 may include a carrier 1201, and a control unit 1252, including an electronics housing 1202 and electronics portion 1205, that may be coupled to carrier 1201.

Carrier 1201 may include a patch configured for adherence to the skin of a subject. Carrier 1201 may be flexible or rigid, or may include flexible or rigid portions. In certain embodiments, carrier 1201 may include a skin patch including a flexible substrate formed of, for example, plastic, silicone, woven natural fibers, and other suitable polymers, copolymers, and combinations thereof. Carrier 1201 may be configured to be affixed or adhered to the skin of a subject through adhesives or other mechanical means. The adhesives may be comprised of biocompatible material, which may allow for the subject or another user to position carrier 1201 at multiple locations on the subject's skin prior to placement of carrier 1201 at a final, desired location.

Carrier 1201 may include or support a plurality of components including, e.g., primary antenna 150, power source 140, and a connector 1203. Primary antenna 150 may include, for example, a double-layer crossover antenna as discussed above. Power source 140, may include, for example, a paper battery, thin film battery, or other type of substantially flat and/or flexible battery. It is contemplated that power source 140 may additionally or alternatively include any other type of battery or power source.

Connector 1203 may be provided on carrier 1201 for coupling electronics housing 1202 to carrier 1201. Connector 1203 may include any suitable mechanical component configured to mount electronics housing 1202. For example, connector 1203 may include a peg, stub, or flexible arm that extends from carrier 1201. Other contemplated connector configurations may include a magnetic connection, a Velcro connection and/or a snap dome connection. While in the exemplary embodiment high in FIG. 11a, connector 1203 is centered on carrier 1201, it is contemplated that connector 1203 may be located on any other portion of carrier 1201. Further, one or more connectors 1203 are contemplated.

In some embodiments, connector 1203 may have a positioning feature for positioning electronics housing 1202 at a specific height, axial location, and/or axial orientation with respect to carrier 1201. For example, connector 1203 may include one or more pegs, rings, boxes, ellipses, bumps, detents, etc., on a portion of or portions of connector 1203. Such elements may engage with corresponding structures associated with housing 1202 such that housing 1202 may be removably secured to carrier 1201 via connector 1203. Connector 1203 may be configured such that removal from electronics housing 1202 may cause breakage of connector 1203. Such a feature may be desirable to prevent re-use of carrier 1201, which may lose efficacy through continued use.

Electronics housing 1202 may be keyed to connector 1203, so that electronics housing 1202 may be selectively mounted on carrier 1201. More particularly, electronics housing 1202 may include a recess 1204 shaped to receive connector 1203. It is contemplated that in some embodiments, recess 1204 may have a shape, size, and/or configuration that is complementary to connector 1203 (e.g., recess 1204 and connector 1203 may have male and female parts) to permit a secure connection between electronics housing 1202 and carrier 1201.

Electronics housing 1202 may further include electronics portion 1205, which may be arranged inside electronics housing 1202 in any manner that is suitable. Electronics portion 1205 may include various components of external unit 120. For example, electronics portion 1205 may include any combination of at least one processor 144 associated with external unit 120, a power source 140, such as a battery, a primary antenna 152, and an electrical circuit 170. Electronics portion 1205 may also include any other component described herein as associated with external unit 120. Additional components may also be recognized by those of skill in the art.

Electronics housing 1202 may further include at least one electrical connector. In the exemplary embodiment, electronics housing may include three electrical connectors 1210, 1211, 1212. Each electrical connector 1210, 1211, 1212 may include a pair of electrical contacts, as shown in FIG. 11b. The pair of electrical contacts of each electrical connector 1210, 1211, 1212 may be continuously electrically connected with each other inside of housing 1202, such that the pair of electrical contacts represents a single connection point to a circuit. In such a configuration, an electrical connection may be established between electronics in housing 1202 even if only one electrode in any of pairs of electrodes 1210, 1211, or 1212 makes contact with an electrical connector associated with carrier 1201, for example. Electrical connectors 1210, 1211, and 1212 may thus constitute redundant electrical contacts. The electrical contacts of each electrical connector 1210, 1211, 1212 may also represent opposite ends of a circuit, for example, the positive and negative ends of a battery charging circuit.

Electrical connectors 1210, 1211, and 1212 may be configured so as to maintain electrical contact with an exposed electrical portion 1108 of primary antenna 140 on carrier 1201 independent of an axial orientation of electronics housing 1202. Connection between any or all of electrical connectors 1210, 1211, 1212 and exposed portions 1108 may thus be established and maintained irrespective of relative axial positions of carrier 1201 and housing 1202. That is, when connector 1203 is received by recess 1204, housing 1202 may rotate with respect to carrier 1201 without interrupting electrical contact between at least one of electrical connectors 1210, 1211, 1212 and exposed electrical portions 1108. Axial orientation independence may be achieved, for example, through the use of circular exposed electrical portions 1108 and each of a pair of contacts of electrical connectors 1210, 1211, 1212 disposed equidistant from a center of recess 1204 at a radius approximately equal to that of a corresponding exposed electrical portion 1108. In this fashion, even if exposed portion 1108 includes a discontinuous circle, at least one electrical contact of electrical connectors 1210, 1211, and 1212 may make contact. In FIG. 11b, electrical connectors 1210, 1211, 1212 are illustrated as pairs of rectangular electrical contacts. Electrical connectors 1210, 1211, 1212, however, may include any number of contacts, be configured as continuous or discontinuous circles, or any other configuration.

In accordance with an exemplary embodiment of the disclosure, processor 144 may be configured to initiate a therapy protocol upon coupling of electronics housing 1202 and carrier 1201. For example, processor 144 may be activated immediately upon coupling electronics housing 1202 to carrier 1201 or at a time after coupling to initiate the therapy protocol. Activation may be manually or automatically achieved.

More particularly, in some embodiments, electronics housing 1202 may include an activator circuit associated with processor 144. In certain embodiments, a user may manually trigger the activator circuit and thus activate processor 144. In other embodiments, the activator circuit may be triggered when at least one electrical connector 1210, 1211, 1212 contacts an exposed electrical portion 108 on carrier 1202. In this manner, simply connecting electronics housing 1202 to carrier 1201 and inducing contact between at least one electrical connector 1210, 1211, 1212 on electronics housing 1202 and an electrode portion 1108 on carrier 1201, may cause processor 144 to automatically activate.

Upon activation, processor 144 may communicate with implant unit 110. Processor 144 may be further configured to generate and deliver one or more therapeutic control signals to implant unit 110 for modulating at least one nerve in the subject's body. These therapeutic control signals will be discussed in more detail below.

In the present disclosure, processor 144 may be configured to delay generation of the therapeutic control signals so that one or more events can occur. For example, processor 144 may be configured to delay the generation of the therapeutic control signals by a predetermined amount of time following the activation of processor 144 so that one or more pre-treatment actions may occur. Such actions may include physical placement of external unit 120 on the subject's body or calibration of control unit 1252 (e.g., calibration of one or more processes or functions provided by processor 144). The delay may also be selected to enable the subject to fall asleep, etc. The subject may initiate the delay, or the delay may automatically occur. The predetermined amount of time may be set by the subject, another person (e.g., the manufacturer or a doctor), or stored as data in a memory accessible by processor 144.

As noted above, in certain embodiments, processor 144 may be configured to delay the generation of the therapeutic control signals to enable physical placement of external unit 120 on the subject's body. The delay may be of sufficient duration to properly position the external unit 120 relative to implant unit 110, and adhere carrier 1201 to the skin of the subject. For example, the delay may be of sufficient duration to enable the subject or another user to position carrier 1201 at multiple locations on the subject's skin prior to placement of carrier 1201 at a final, desired location. The final location may be on, for example, the neck, head, and/or chin of the subject. In such embodiments, a delay period sufficient to enable positioning of external unit 120 may be set at 30 seconds, 1 minute, 2 minutes, 5 minutes, 10 minutes, or at any other suitable duration.

In some embodiments, processor 144 may be configured to generate signals indicative of the placement or location of external unit 120 relative to implant 110. Alternatively, processor 144 may receive signals from implant unit 110 indicative of the placement or location of external unit relative to implant unit 110 or that can be used to determine such placement or location. The subject or another person may position carrier 1201 at a location on the subject's body based on feedback (e.g., a visual indicator, audible indicator, haptic indicator, or any other suitable indication) associated with the determined location or relative orientation between implant unit 110 and external unit 120. Processor 144 may be further configured to emit a control signal (e.g., a sub-modulation control signal having an amplitude, duration, etc. selected so as to fall below a stimulation threshold for a nerve or nerve tissue) in order to determine the location of implant unit 110 relative to external unit 120. Processor 144 may be configured to discontinue the control signal after the carrier has been affixed or adhered to subject's skin at a desired location.

In certain other embodiments, processor 144 may be configured to delay the generation of the therapeutic control signals to enable calibration of control unit 1252 including components (e.g., processor 144) of control unit 1252. The delay may be of sufficient duration such that the calibration procedure occurs over a time duration equal to or less than the selected delay period. In some embodiments, the calibration delay period may extend for a few microseconds, a few milliseconds, 1 second, 5 seconds, or over any other suitable time duration. If two or more processors are included in electronics housing 1202, the delay may be of sufficient duration so that both processors may be calibrated within a single delay period.

In yet other embodiments, processor 144 may be configured to delay the generation of the therapeutic control signals to enable the subject to fall asleep. For example, the duration of the delay may be in the range of about 15 minutes to about 90 minutes. In preferred embodiments, the delay may be in the range of about 30 minutes to about 90 minutes. In some embodiments, especially in view of experimental results indicating that the patients do not perceive the modulation events, a waiting period for allowing the subject to fall asleep may not be required. In such embodiments, the predetermined amount of time may be zero i.e., processor 144 may immediately enable generation of the modulation signals.

It is contemplated that the delay may be of sufficient duration to enable two or more of the actions discussed above to occur. It is further contemplated that the delay may be of sufficient duration to enable three or more actions to occur following activation of processor 144. In certain embodiments no delay may be required, and therefore no delay may occur.

Figure 4:
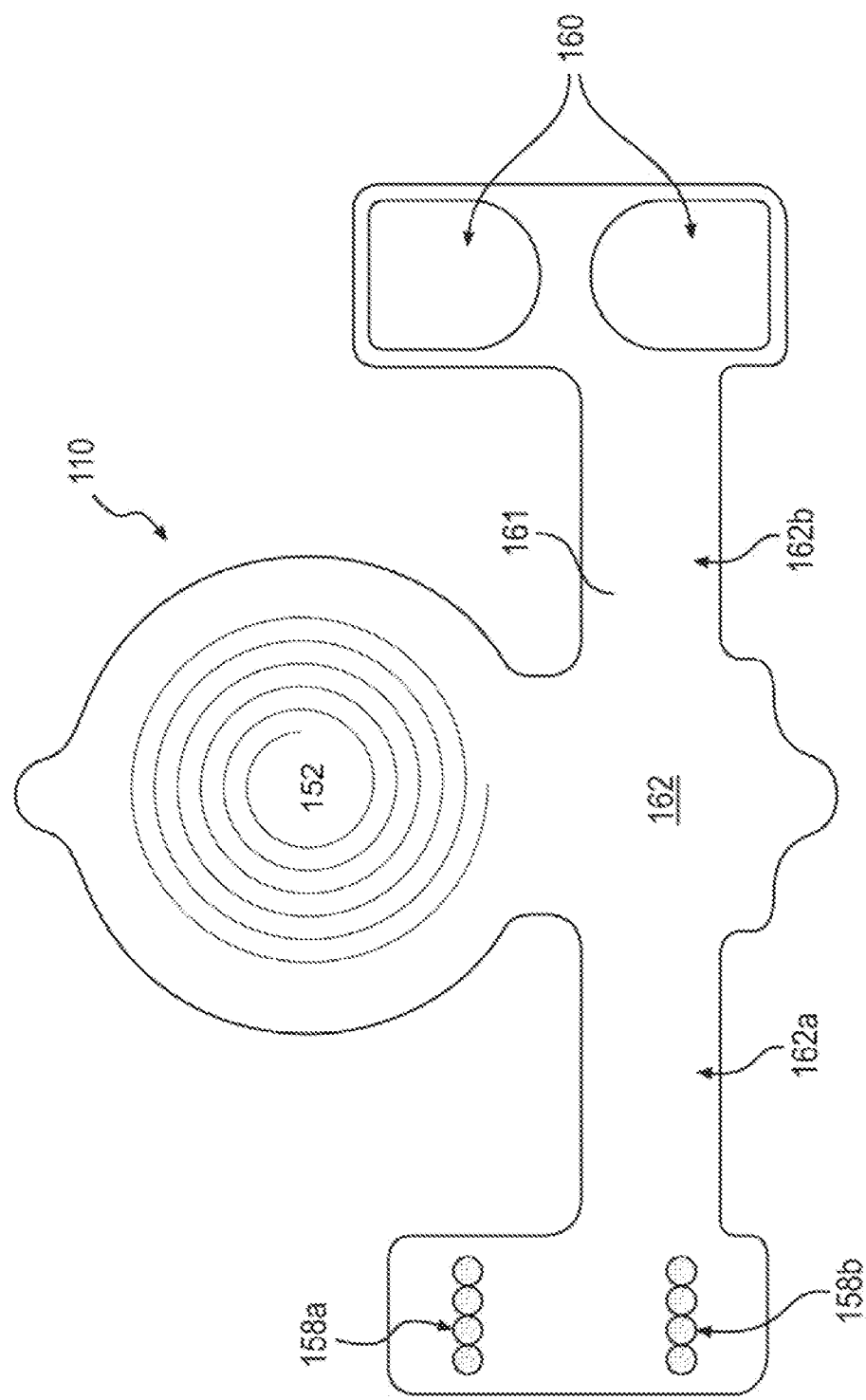
FIG. 4 is a top view of an implant unit, according to an exemplary embodiment of the present disclosure.

Returning to FIG. 4, implant unit 110 may include a plurality of field-generating implant electrodes 158a, 158b. The electrodes may include any suitable shape and/or orientation on the implant unit so long as the electrodes may be configured to generate an electric field in the body of a patient. Implant electrodes 158a and 158b may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, circular electrodes, and/or circular pairs of electrodes. As shown in FIG. 4, electrodes 158a and 158b may be located on an end of a first extension 162a of an elongate arm 162. The electrodes, however, may be located on any portion of implant unit 110. Additionally, implant unit 110 may include electrodes located at a plurality of locations, for example on an end of both a first extension 162a and a second extension 162b of elongate arm 162, as illustrated, for example, in FIG. 5. Implant electrodes may have a thickness between about 200 nanometers and 1 millimeter. Anode and cathode electrode pairs may be spaced apart by about a distance of about 0.2 mm to 25 mm. In additional embodiments, anode and cathode electrode pairs may be spaced apart by a distance of about 1 mm to 10 mm, or between 4 mm and 7 mm. Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm and 1 mm.

FIG. 4 provides a schematic representation of an exemplary configuration of implant unit 110. As illustrated in FIG. 4, in one embodiment, the field-generating electrodes 158a and 158b may include two sets of four circular electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include, for example, elongated arms, suture holes, polymeric surgical mesh, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body. For example, in some embodiments, implant unit 110 may include an elongate arm 162 having a first extension 162a and, optionally, a second extension 162b. Extensions 162a and 162b may aid in orienting implant unit 110 with respect to a particular muscle (e.g., the genioglossus muscle), a nerve within a patient's body, or a surface within a body above a nerve. For example, first and second extensions 162a, 162b may be configured to enable the implant unit to conform at least partially around soft or hard tissue (e.g., nerve, bone, or muscle, etc.) beneath a patient's skin. Further, implant unit 110 may also include one or more suture holes 160 located anywhere on flexible carrier 161. For example, in some embodiments, suture holes 160 may be placed on second extension 162b of elongate arm 162 and/or on first extension 162a of elongate arm 162. Implant unit 110 may be constructed in various shapes. Additionally, or alternatively, implant unit 110 may include surgical mesh 1050 or other perforatable material. In some embodiments, implant unit may appear substantially as illustrated in FIG. 4. In other embodiments, implant unit 110 may lack illustrated structures such as second extension 162b, or may have additional or different structures in different orientations. Additionally, implant unit 110 may be formed with a generally triangular, circular, or rectangular shape, as an alternative to the winged shape shown in FIG. 4. In some embodiments, the shape of implant unit 110 (e.g., as shown in FIG. 4) may facilitate orientation of implant unit 110 with respect to a particular nerve to be modulated. Thus, other regular or irregular shapes may be adopted in order to facilitate implantation in differing parts of the body.

Figure 5:
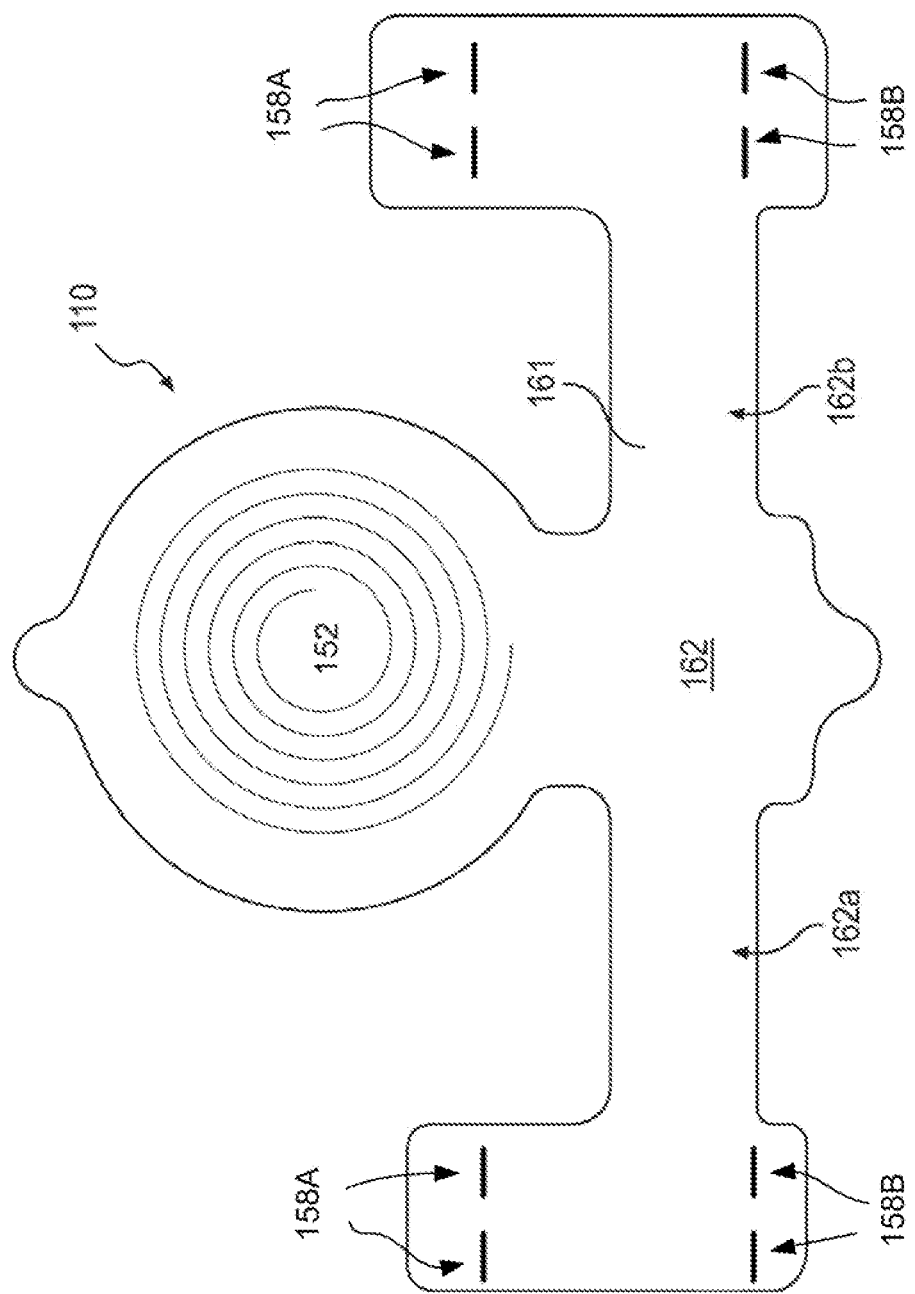
FIG. 5 is a top view of an alternate embodiment of an implant unit, according to an exemplary embodiment of the present disclosure.

As illustrated in FIG. 4, secondary antenna 152 and electrodes 158a, 158b may be mounted on or integrated with flexible carrier 161. Various circuit components and connecting wires (discussed further below) may be used to connect secondary antenna with implant electrodes 158a and 158b. To protect the antenna, electrodes, circuit components, and connecting wires from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include a plurality of layers, including different materials or combinations of materials in different layers FIG. 5 is a perspective view of an alternate embodiment of an implant unit 110, according to an exemplary embodiment of the present disclosure. As illustrated in FIG. 5, implant unit 110 may include a plurality of electrodes, located, for example, at the ends of first extension 162a and second extension 162b. In this embodiment, implant electrodes 158a and 158b are short line electrodes.

Returning to FIGS. 2 and 3, external unit 120 may be configured to communicate with implant unit 110. For example, in some embodiments, a primary signal may be generated on primary antenna 150, using, e.g., processor 144, signal source 142, and amplifier 146. More specifically, in one embodiment, power source 140 may be configured to provide power to one or both of the processor 144 and the signal source 142. The processor 144 may be configured to cause signal source 142 to generate a signal (e.g., an RF energy signal). Signal source 142 may be configured to output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), a desired magnitude of electric field to be generated by implant electrodes 158a, 158b, etc. Amplifier 146 may output the amplified signal to primary antenna 150.

External unit 120 may communicate a primary signal on primary antenna to the secondary antenna 152 of implant unit 110. This communication may result from coupling between primary antenna 150 and secondary antenna 152. Such coupling of the primary antenna and the secondary antenna may include any interaction between the primary antenna and the secondary antenna that causes a signal on the secondary antenna in response to a signal applied to the primary antenna. In some embodiments, coupling between the primary and secondary antennas may include capacitive coupling, inductive coupling, radiofrequency coupling, etc. and any combinations thereof.

Coupling between primary antenna 150 and secondary antenna 152 may depend on the proximity of the primary antenna relative to the secondary antenna. That is, in some embodiments, an efficiency or degree of coupling between primary antenna 150 and secondary antenna 152 may depend on the proximity of the primary antenna to the secondary antenna. The proximity of the primary and secondary antennas may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of a primary signal on primary antenna 150 may cause or induce a secondary signal on secondary antenna 152, the coupling between the two antennas may also lead to a coupled signal or signal components on the primary antenna 150 as a result of the secondary signal present on secondary antenna 152. A signal on primary antenna 150 induced by a secondary signal on secondary antenna 152 may be referred to as a primary coupled signal component. The primary signal may refer to any and all signals or signal components present on primary antenna 150, regardless of source, and the primary coupled signal component may refer to any signal or signal component arising on the primary antenna as a result of coupling with signals present on secondary antenna 152. Thus, in some embodiments, the primary coupled signal component may contribute to the primary signal on primary antenna 150.

Implant unit 110 may be configured to respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158a and 158b.

Figure 6:
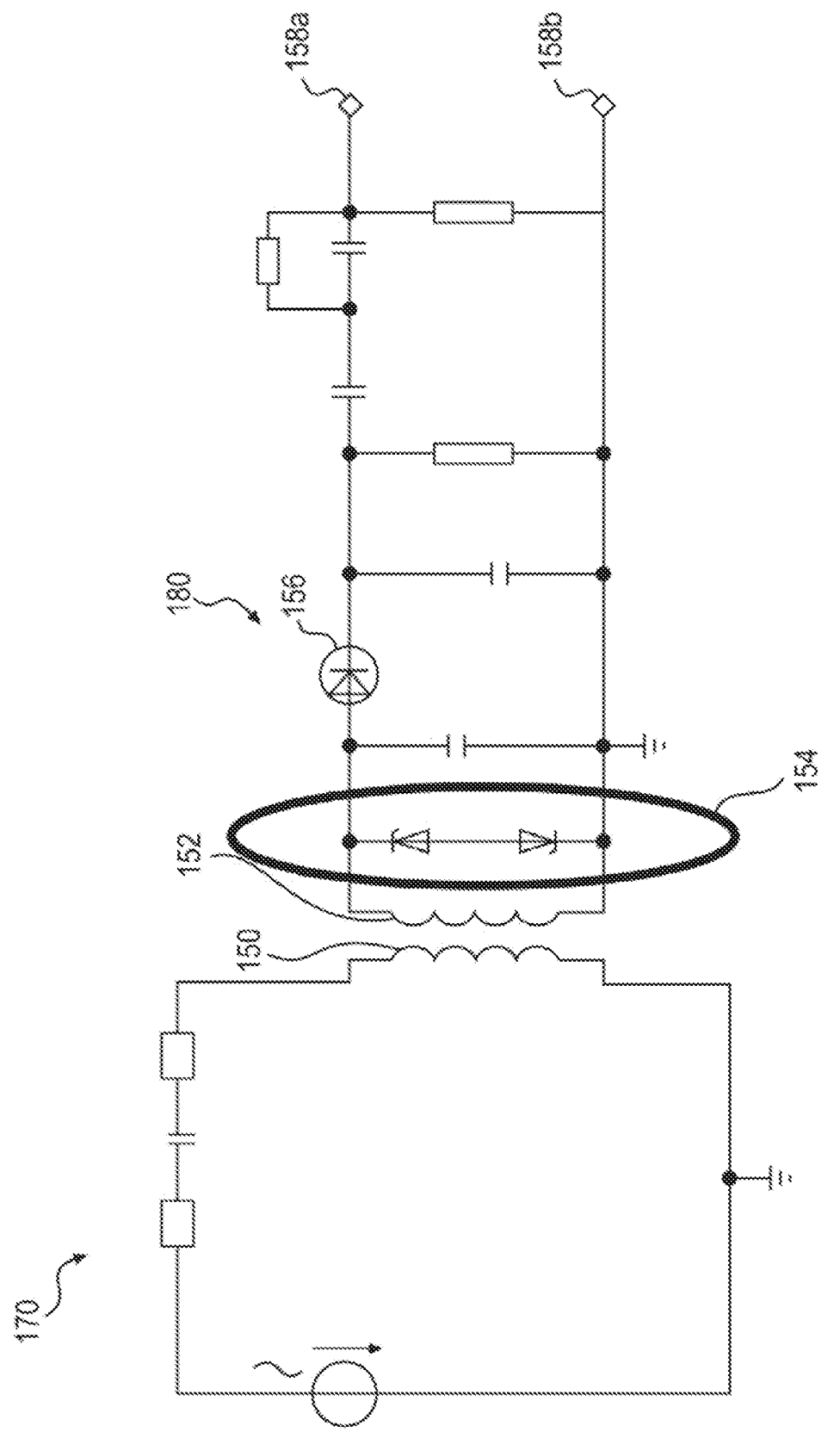
FIG. 6 illustrates circuitry of an implant unit and an external unit, according to an exemplary embodiment of the present disclosure.

FIG. 6 illustrates circuitry 170 that may be included in external unit 120 and circuitry 180 that may be included in implant unit 110. Additional, different, or fewer circuit components may be included in either or both of circuitry 170 and circuitry 180. As shown in FIG. 6, secondary antenna 152 may be arranged in electrical communication with implant electrodes 158a, 158b. In some embodiments, circuitry connecting secondary antenna 152 with implant electrodes 158a and 158b may cause a voltage potential across implant electrodes 158a and 158b in the presence of a secondary signal on secondary antenna 152. This voltage potential may be referred to as a field inducing signal, as this voltage potential may generate an electric field between implant electrodes 158a and 158b. More broadly, the field inducing signal may include any signal (e.g., voltage potential) applied to electrodes associated with the implant unit that may result in an electric field being generated between the electrodes.

The field inducing signal may be generated as a result of conditioning of the secondary signal by circuitry 180. As shown in FIG. 6, circuitry 170 of external unit 120 may be configured to generate an AC primary signal on primary antenna 150 that may cause an AC secondary signal on secondary antenna 152. In certain embodiments, however, it may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158a and 158b.

As noted above, the field inducing signal may be configured to generate an electric field between implant electrodes 158a and 158b. In some instances, the magnitude and/or duration of the generated electric field resulting from the field inducing signal may be sufficient to modulate one or more nerves in the vicinity of electrodes 158a and 158b. In such cases, the field inducing signal may be referred to as a modulation signal. In other instances, the magnitude and/or duration of the field inducing signal may generate an electric field that does not result in nerve modulation. In such cases, the field inducing signal may be referred to as a sub-modulation signal.

Various types of field inducing signals may constitute modulation signals. For example, in some embodiments, a modulation signal may include a moderate amplitude and moderate duration, while in other embodiments, a modulation signal may include a higher amplitude and a shorter duration. Various amplitudes and/or durations of field-inducing signals across electrodes 158a, 158b may result in modulation signals, and whether a field-inducing signal rises to the level of a modulation signal can depend on many factors (e.g., distance from a particular nerve to be stimulated; whether the nerve is branched; orientation of the induced electric field with respect to the nerve; type of tissue present between the electrodes and the nerve; etc.).

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158a and 158b).

Processor 144 may be configured to limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. Processor 144 may be configured to account for such limitations when setting the magnitude and/or duration of a primary signal to be applied to primary antenna 150.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals).

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also be configured to cause application of sub-modulation control signals to primary antenna 150. Such sub-modulation control signals may include an amplitude and/or duration that result in a sub-modulation signal at electrodes 158a, 158b. While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, induces a primary coupled signal component on primary antenna 150.

To analyze the primary coupled signal component induced on primary antenna 150, external unit 120 may include a feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary coupled signal component on primary antenna 150.

The primary coupled signal component may be fed to processor 144 by feedback circuit 148 and may be used as a basis for determining a degree of coupling between primary antenna 150 and secondary antenna 152. The degree of coupling may enable determination of the efficacy of the energy transfer between two antennas. Processor 144 may also use the determined degree of coupling in regulating delivery of power to implant unit 110.

Processor 144 may be configured with any suitable logic for determining how to regulate power transfer to implant unit 110 based on the determined degree of coupling. For example, where the primary coupled signal component indicates that a degree of coupling has changed from a baseline coupling level, processor 144 may determine that secondary antenna 152 has moved with respect to primary antenna 150 (either in coaxial offset, lateral offset, or angular offset, or any combination). Such movement, for example, may be associated with a movement of implant unit 110, and the tissue that it is associated with based on its implant location. Thus, in such situations, processor 144 may determine that modulation of a nerve in the patient's body is appropriate. More particularly, in response to an indication of a change in coupling, processor 144, in some embodiments, may cause application of a modulation control signal to primary antenna 150 in order to generate a modulation signal at implant electrodes 158a, 158b, e.g., to cause modulation of a nerve of the patient.

In an embodiment for the treatment of OSA, movement of implant unit 110 may be associated with movement of the tongue, which may indicate the onset of a sleep apnea event or a sleep apnea precursor. The onset of a sleep apnea event of sleep apnea precursor may require the stimulation of the genioglossus muscle of the patient to relieve or avert the event. Such stimulation may result in contraction of the muscle and movement of the patient's tongue away from the patient's airway.

In embodiments for the treatment of head pain, including migraines, processor 144 may be configured to generate a modulation control signal based on a signal from a user, for example, or a detected level of neural activity in a sensory neuron (e.g. the greater occipital nerve or trigeminal nerve) associated with head pain. A modulation control signal generated by the processor and applied to the primary antenna 150 may generate a modulation signal at implant electrodes 158a, 158b, e.g., to cause inhibition or blocking of a sensory nerve of the patient. Such inhibition or blocking may decrease or eliminate the sensation of pain for the patient.

In embodiments for the treatment of hypertension, processor 144 may be configured to generate a modulation control signal based on, for example, pre-programmed instructions and/or signals from an implant indicative of blood pressure. A modulation control signal generated by processor 144 and applied to the primary antenna 150 may generate a modulation signal at implant electrodes 158a, 158b, e.g., to cause either inhibition or stimulation of nerve of a patient, depending on the requirements. For example, a neuromodulator placed in a carotid artery or jugular artery (i.e. in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator place in a renal artery may receive a modulation control signal tailored to cause an inhibiting or blocking signal at the electrodes, thereby inhibiting a signal to raise blood pressure carried from the renal nerves to the kidneys.

Modulation control signals may include stimulation control signals, and sub-modulation control signals may include sub-stimulation control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

In some embodiments, stimulation control signals may include a pulse train, wherein each pulse includes a plurality of sub-pulses. An alternating current signal (e.g., at a frequency of between about 6.5-13.6 MHz) may be used to generate the pulse train, as follows. A sub-pulse may have a duration of between 50-250 microseconds, or a duration of between 1 microsecond and 2 milliseconds, during which an alternating current signal is turned on. For example, a 200 microsecond sub-pulse of a 10 MHz alternating current signal will include approximately 2000 periods. Each pulse may, in turn, have a duration of between 100 and 500 milliseconds, during which sub-pulses occur at a frequency of between 25 and 100 Hz. For example, a 200 millisecond pulse of 50 Hz sub-pulses will include approximately 10 sub-pulses. Finally, in a pulse train, each pulse may be separated from the next by a duration of between 0.2 and 2 seconds. For example, in a pulse train of 200 millisecond pulses, each separated by 1.3 seconds from the next, a new pulse will occur every 1.5 seconds. A pulse train of this embodiment may be utilized, for example, to provide ongoing stimulation during a treatment session. In the context of OSA, a treatment session may be a period of time during which a subject is asleep and in need of treatment to prevent OSA. Such a treatment session may last anywhere from about three to ten hours. In the context of other conditions to which neural modulators of the present disclosure are applied, a treatment session may be of varying length according to the duration of the treated condition.

Processor 144 may be configured to determine a degree of coupling between primary antenna 150 and secondary antenna 152 by monitoring one or more aspects of the primary coupled signal component received through feedback circuit 148. In some embodiments, processor 144 may determine a degree of coupling between primary antenna 150 and secondary antenna 152 by monitoring a voltage level associated with the primary coupled signal component, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary coupled signal component. This baseline voltage level, for example, may be associated with a range of movement of the patient's tongue when a sleep apnea event or its precursor is not occurring, e.g. during normal breathing. As the patient's tongue moves toward a position associated with a sleep apnea event or its precursor, the coaxial, lateral, or angular offset between primary antenna 150 and secondary antenna 152 may change. As a result, the degree of coupling between primary antenna 150 and secondary antenna 152 may change, and the voltage level or current level of the primary coupled signal component on primary antenna 150 may also change. Processor 144 may be configured to recognize a sleep apnea event or its precursor when a voltage level, current level, or other electrical characteristic associated with the primary coupled signal component changes by a predetermined amount or reaches a predetermined absolute value.

Figure 7:
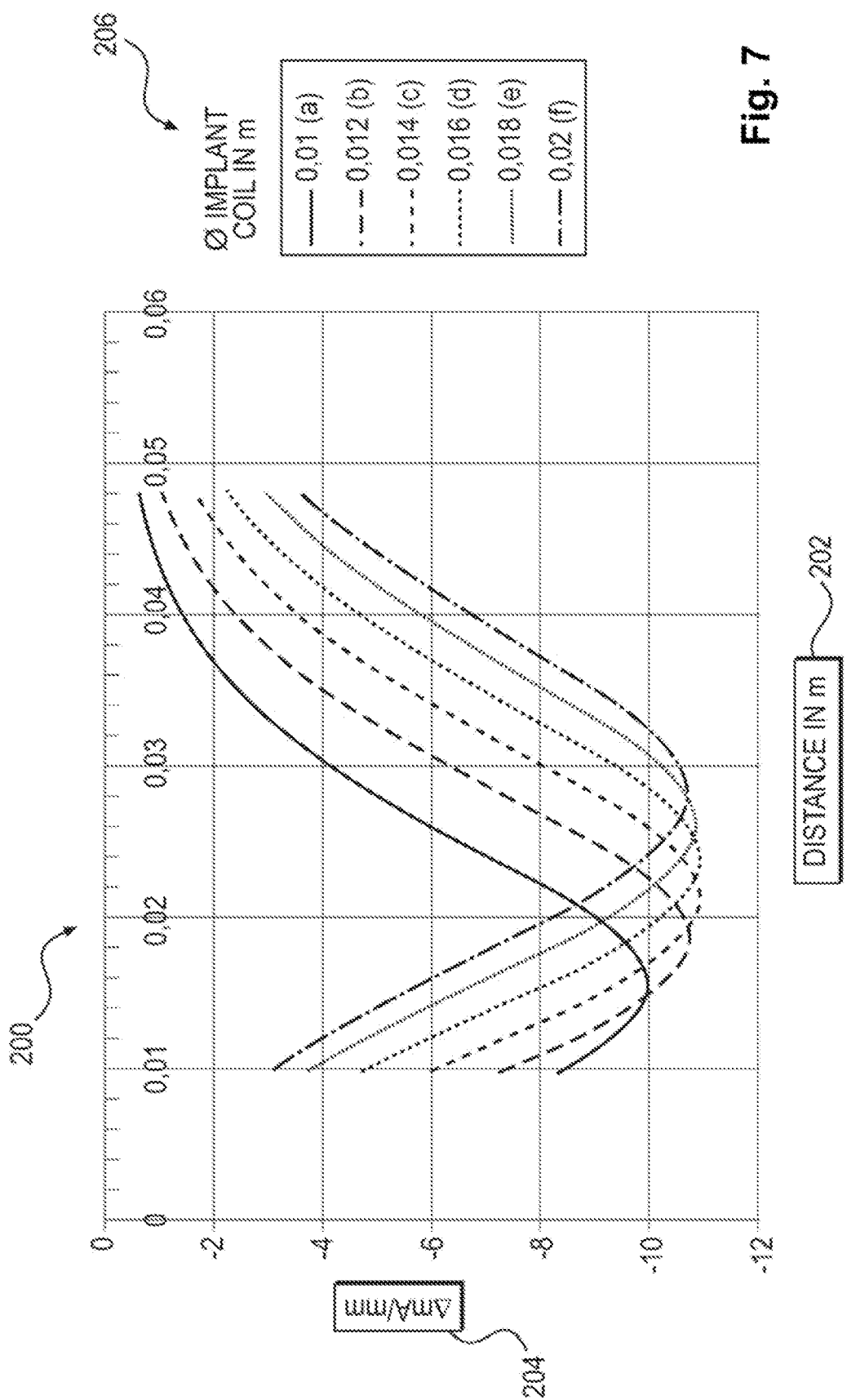
FIG. 7 illustrates a graph of quantities that may be used in determining energy delivery as a function coupling, according to exemplary embodiments of the present disclosure.

FIG. 7 provides a graph that illustrates this principle in more detail. For a two-coil system where one coil receives a radio frequency (RF) drive signal, graph 200 plots a rate of change in induced current in the receiving coil as a function of coaxial distance between the coils. For various coil diameters and initial displacements, graph 200 illustrates the sensitivity of the induced current to further displacement between the coils, moving them either closer together or further apart. It also indicates that, overall, the induced current in the secondary coil will decrease as the secondary coil is moved away from the primary, drive coil, i.e. the rate of change of induced current, in mA/mm, is consistently negative. The sensitivity of the induced current to further displacement between the coils varies with distance. For example, at a separation distance of 10 mm, the rate of change in current as a function of additional displacement in a 14 mm coil is approximately −6 mA/mm. If the displacement of the coils is approximately 22 mm, the rate of change in the induced current in response to additional displacement is approximately −11 mA/mm, which corresponds to a local maximum in the rate of change of the induced current. Increasing the separation distance beyond 22 mm continues to result in a decline in the induced current in the secondary coil, but the rate of change decreases. For example, at a separation distance of about 30 mm, the 14 mm coil experiences a rate of change in the induced current in response to additional displacement of about −8 mA/mm. With this type of information, processor 144 may be able to determine a particular degree of coupling between primary antenna 150 and secondary antenna 152, at any given time, by observing the magnitude and/or rate of change in the magnitude of the current associated with the primary coupled signal component on primary antenna 150.

Processor 144 may be configured to determine a degree of coupling between primary antenna 150 and secondary antenna 152 by monitoring other aspects of the primary coupled signal component. For example, in some embodiments, the non-linear behavior of circuitry 180 in implant unit 110 may be monitored to determine a degree of coupling. For example, the presence, absence, magnitude, reduction and/or onset of harmonic components in the primary coupled signal component on primary antenna 150 may reflect the behavior of circuitry 180 in response to various control signals (either sub-modulation or modulation control signals) and, therefore, may be used to determine a degree of coupling between primary antenna 150 and secondary antenna 152.

As shown in FIG. 6, circuitry 180 in implant unit 110 may constitute a non-linear circuit due, for example, to the presence of non-linear circuit components, such as diode 156. Such non-linear circuit components may induce non-linear voltage responses under certain operation conditions. Non-linear operation conditions may be induced when the voltage potential across diode 156 exceeds the activation threshold for diode 156. Thus, when implant circuitry 180 is excited at a particular frequency, this circuit may oscillate at multiple frequencies. Spectrum analysis of the secondary signal on secondary antenna 152, therefore, may reveal one or more oscillations, called harmonics, that appear at certain multiples of the excitation frequency. Through coupling of primary antenna 150 and secondary antenna 152, any harmonics produced by implant circuitry 180 and appearing on secondary antenna 152 may also appear in the primary coupled signal component present on primary antenna 150.

In certain embodiments, circuitry 180 may include additional circuit components that alter the characteristics of the harmonics generated in circuitry 180 above a certain transition point. Monitoring how these non-linear harmonics behave above and below the transition point may enable a determination of a degree of coupling between primary antenna 150 and secondary antenna 152. For example, as shown in FIG. 6, circuitry 180 may include a harmonics modifier circuit 154, which may include any electrical components that non-linearly alter the harmonics generated in circuitry 180. In some embodiments, harmonics modifier circuit 154 may include a pair of Zener diodes. Below a certain voltage level, these Zener diodes remain forward biased such that no current will flow through either diode. Above the breakdown voltage of the Zener diodes, however, these devices become conductive in the reversed biased direction and will allow current to flow through harmonics modifier circuit 154. Once the Zener diodes become conductive, they begin to affect the oscillatory behavior of circuitry 180, and, as a result, certain harmonic oscillation frequencies may be affected (e.g., reduced in magnitude).

Figure 8:
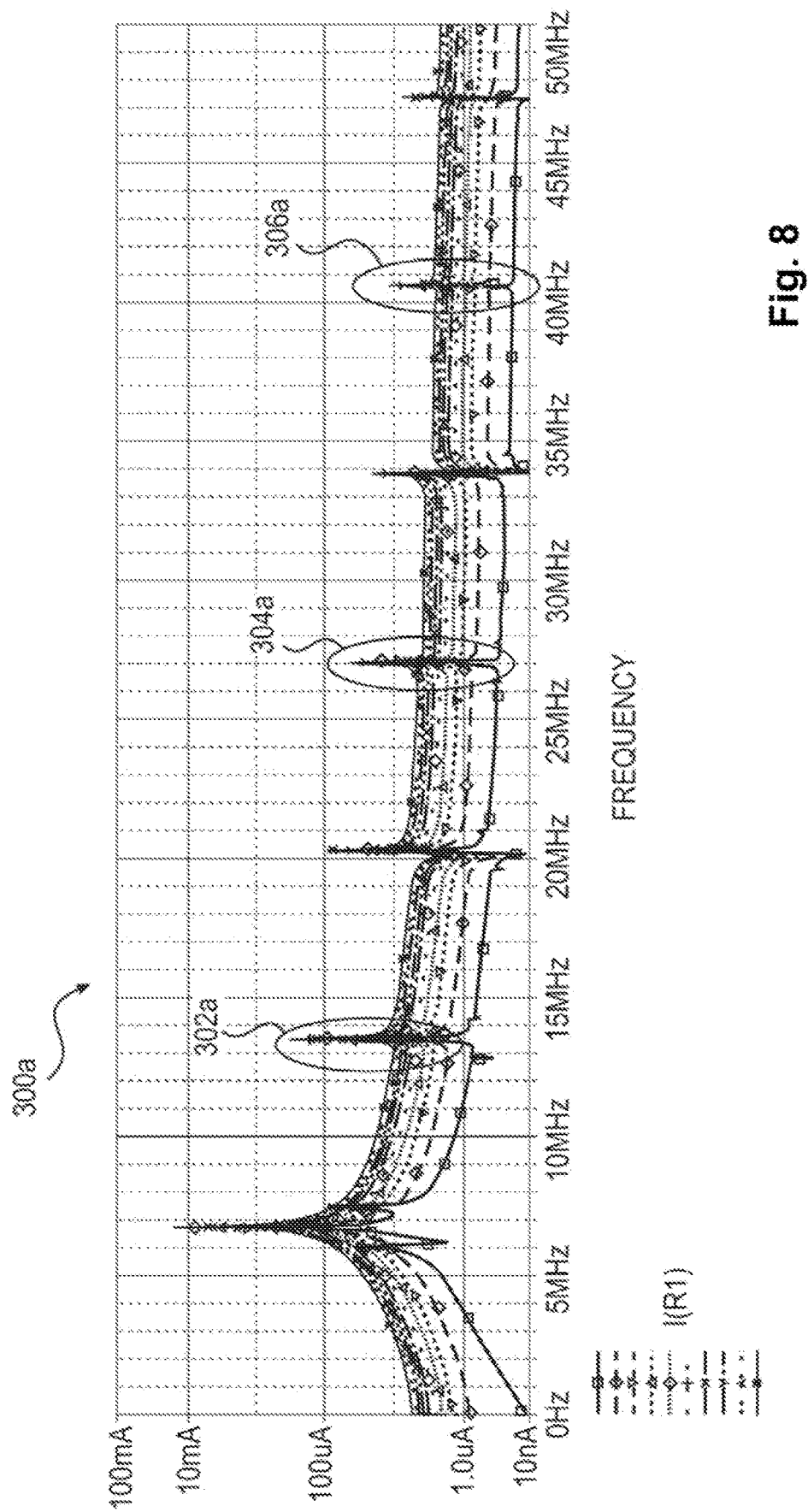
FIG. 8 depicts a graph illustrating non-linear harmonics, according to exemplary embodiments of the present disclosure.
Figure 9:
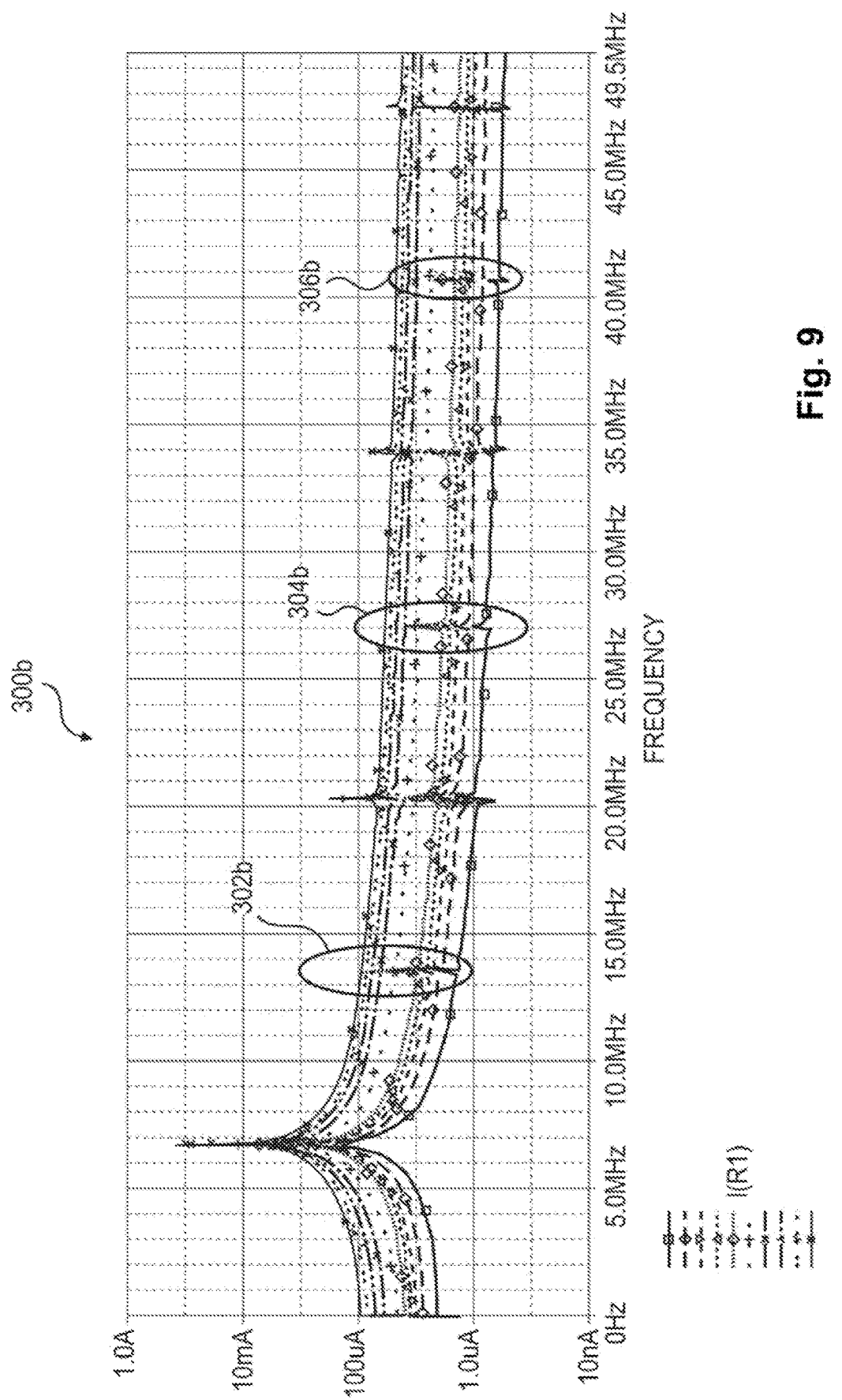
FIG. 9 depicts a graph of quantities that may be used in determining energy delivery as a function coupling, according to exemplary embodiments of the present disclosure.

FIGS. 8 and 9 illustrate this effect. For example, FIG. 8 illustrates a graph 300a that shows the oscillatory behavior of circuitry 180 at several amplitudes ranging from about 10 nanoamps to about 20 microamps. As shown, the primary excitation frequency occurs at about 6.7 MHz and harmonics appear both at even and odd multiples of the primary excitation frequency. For example, even multiples appear at twice the excitation frequency (peak 302a), four times the excitation frequency (peak 304a) and six times the excitation frequency (peak 306a). As the amplitude of the excitation signal rises between 10 nanoamps and 40 microamps, the amplitude of peaks 302a, 304a, and 306a all increase.

FIG. 9 illustrates the effect on the even harmonic response of circuitry 180 caused by harmonics modifier circuit 154. FIG. 9 illustrates a graph 300*b* that shows the oscillatory behavior of circuitry 180 at several amplitudes ranging from about 30 microamps to about 100 microamps. As in FIG. 8, FIG. 9 shows a primary excitation frequency at about 6.7 MHz and second, fourth, and sixth order harmonics (peaks 302*b*, 304*b*, and 306*b*, respectively) appearing at even multiples of the excitation frequency. As the amplitude of the excitation signal rises, however, between about 30 microamps to about 100 microamps, the amplitudes of peaks 302*b*, 304*b*, and 306*b* do not continuously increase. Rather, the amplitude of the second order harmonics decreases rapidly above a certain transition level (e.g., about 80 microamps in FIG. 8). This transition level corresponds to the level at which the Zener diodes become conductive in the reverse biased direction and begin to affect the oscillatory behavior of circuitry 180.

Monitoring the level at which this transition occurs may enable a determination of a degree of coupling between primary antenna 150 and secondary antenna 152. For example, in some embodiments, a patient may attach external unit 120 over an area of the skin under which implant unit 110 resides. Processor 144 can proceed to cause a series of sub-modulation control signals to be applied to primary antenna 150, which in turn cause secondary signals on secondary antenna 152. These sub-modulation control signals may progress over a sweep or scan of various signal amplitude levels. By monitoring the resulting primary coupled signal component on primary antenna 150 (generated through coupling with the secondary signal on secondary antenna 152), processor 144 can determine the amplitude of primary signal (whether a sub-modulation control signal or other signal) that results in a secondary signal of sufficient magnitude to activate harmonics modifier circuit 154. That is, processor 144 can monitor the amplitude of the second, fourth, or sixth order harmonics and determine the amplitude of the primary signal at which the amplitude of any of the even harmonics drops. FIGS. 8 and 9 illustrate the principles of detecting coupling through the measurement of non-linear harmonics. These figures illustrate data based around a 6.7 MHz excitation frequency. These principles, however, are not limited to the 6.7 MHz excitation frequency illustrated, and may be used with a primary signal of any suitable frequency.

In some embodiments, the determined amplitude of the primary signal corresponding to the transition level of the Zener diodes (which may be referred to as a primary signal transition amplitude) may establish a baseline range when the patient attaches external unit 120 to the skin. Presumably, while the patient is awake, the tongue is not blocking the patient's airway and moves with the patients breathing in a natural range, where coupling between primary antenna 150 and secondary antenna 152 may be within a baseline range. A baseline coupling range may encompass a maximum coupling between primary antenna 150 and secondary antenna 152. A baseline coupling range may also encompass a range that does not include a maximum coupling level between primary antenna 150 and secondary antenna 152. Thus, the initially determined primary signal transition amplitude may be fairly representative of a non-sleep apnea condition and may be used by processor 144 as a baseline in determining a degree of coupling between primary antenna 150 and secondary antenna 152. Optionally, processor 144 may also be configured to monitor the primary signal transition amplitude over a series of scans and select the minimum value as a baseline, as the minimum value may correspond to a condition of maximum coupling between primary antenna 150 and secondary antenna 152 during normal breathing conditions.

As the patient wears external unit 120, processor 144 may periodically scan over a range of primary signal amplitudes to determine a current value of the primary signal transition amplitude. In some embodiments, the range of amplitudes that processor 144 selects for the scan may be based on (e.g., near) the level of the baseline primary signal transition amplitude. If a periodic scan results in determination of a primary signal transition amplitude different from the baseline primary signal transition amplitude, processor 144 may determine that there has been a change from the baseline initial conditions. For example, in some embodiments, an increase in the primary signal transition amplitude over the baseline value may indicate that there has been a reduction in the degree of coupling between primary antenna 150 and secondary antenna 152 (e.g., because the implant has moved or an internal state of the implant has changed).

In addition to determining whether a change in the degree of coupling has occurred, processor 144 may also be configured to determine a specific degree of coupling based on an observed primary signal transition amplitude. For example, in some embodiments, processor 144 may have access to a lookup table or a memory storing data that correlates various primary signal transition amplitudes with distances (or any other quantity indicative of a degree of coupling) between primary antenna 150 and secondary antenna 152. In other embodiments, processor 144 may be configured to calculate a degree of coupling based on performance characteristics of known circuit components.

By periodically determining a degree of coupling value, processor 144 may be configured to determine, in situ, appropriate parameter values for the modulation control signal that will ultimately result in nerve modulation. For example, by determining the degree of coupling between primary antenna 150 and secondary antenna 152, processor 144 may be configured to select characteristics of the modulation control signal (e.g., amplitude, pulse duration, frequency, etc.) that may provide a modulation signal at electrodes 158*a*, 158*b* in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

Additionally or alternatively, processor 144 may be configured to determine the degree of coupling between primary antenna 150 and secondary antenna 152 during modulation. The tongue, or other structure on or near which the implant is located, and thus implant unit 110, may move as a result of modulation. Thus, the degree of coupling may change during modulation. Processor 144 may be configured to determine the degree of coupling as it changes during modulation, in order to dynamically adjust characteristics of the modulation control signal according to the changing degree of coupling. This adjustment may permit processor 144 to cause implant unit 110 to provide an appropriate modulation signal at electrodes 158*a*, 158*b* throughout a modulation event. For example, processor 144 may alter the primary signal in accordance with the changing degree of coupling in order to maintain a constant modulation signal, or to cause the modulation signal to be reduced in a controlled manner according to patient needs.

More particularly, the response of processor 144 may be correlated to the determined degree of coupling. In situations where processor 144 determines that the degree of coupling between primary antenna 150 and secondary antenna has fallen only slightly below a predetermined coupling threshold (e.g., during snoring or during a small vibration of the tongue or other sleep apnea event precursor), processor 144 may determine that only a small response is necessary. Thus, processor 144 may select modulation control signal parameters that will result in a relatively small response (e.g., a short stimulation of a nerve, small muscle contraction, etc.). Where, however, processor 144 determines that the degree of coupling has fallen substantially below the predetermined coupling threshold (e.g., where the tongue has moved enough to cause a sleep apnea event), processor 144 may determine that a larger response is required. As a result, processor 144 may select modulation control signal parameters that will result in a larger response. In some embodiments, only enough power may be transmitted to implant unit 110 to cause the desired level of response. In other words, processor 144 may be configured to cause a metered response based on the determined degree of coupling between primary antenna 150 and secondary antenna 152. As the determined degree of coupling decreases, processor 144 may cause transfer of power in increasing amounts. Such an approach may preserve battery life in the external unit 120, may protect circuitry 170 and circuitry 180, may increase effectiveness in addressing the type of detected condition (e.g., sleep apnea, snoring, tongue movement, etc.), and may be more comfortable for the patient.

In some embodiments, processor 144 may employ an iterative process in order to select modulation control signal parameters that result in a desired response level. For example, upon determining that a modulation control signal should be generated, processor 144 may cause generation of an initial modulation control signal based on a set of predetermined parameter values. If feedback from feedback circuit 148 indicates that a nerve has been modulated (e.g., if an increase in a degree of coupling is observed), then processor 144 may return to a monitoring mode by issuing sub-modulation control signals. If, on the other hand, the feedback suggests that the intended nerve modulation did not occur as a result of the intended modulation control signal or that modulation of the nerve occurred but only partially provided the desired result (e.g., movement of the tongue only partially away from the airway), processor 144 may change one or more parameter values associated with the modulation control signal (e.g., the amplitude, pulse duration, etc.).

Where no nerve modulation occurred, processor 144 may increase one or more parameters of the modulation control signal periodically until the feedback indicates that nerve modulation has occurred. Where nerve modulation occurred, but did not produce the desired result, processor 144 may re-evaluate the degree of coupling between primary antenna 150 and secondary antenna 152 and select new parameters for the modulation control signal targeted toward achieving a desired result. For example, where stimulation of a nerve causes the tongue to move only partially away from the patient's airway, additional stimulation may be desired. Because the tongue has moved away from the airway, however, implant unit 110 may be closer to external unit 120 and, therefore, the degree of coupling may have increased. As a result, to move the tongue a remaining distance to a desired location may require transfer to implant unit 110 of a smaller amount of power than what was supplied prior to the last stimulation-induced movement of the tongue. Thus, based on a newly determined degree of coupling, processor 144 can select new parameters for the stimulation control signal aimed at moving the tongue the remaining distance to the desired location.

In one mode of operation, processor 144 may be configured to sweep over a range of parameter values until nerve modulation is achieved. For example, in circumstances where an applied sub-modulation control signal results in feedback indicating that nerve modulation is appropriate, processor 144 may use the last applied sub-modulation control signal as a starting point for generation of the modulation control signal. The amplitude and/or pulse duration (or other parameters) associated with the signal applied to primary antenna 150 may be iteratively increased by predetermined amounts and at a predetermined rate until the feedback indicates that nerve modulation has occurred.

Processor 144 may be configured to determine or derive various physiologic data based on the determined degree of coupling between primary antenna 150 and secondary antenna 152. For example, in some embodiments the degree of coupling may indicate a distance between external unit 120 and implant unit 110, which processor 144 may use to determine a position of external unit 120 or a relative position of a patient's tongue. Monitoring the degree of coupling can also provide such physiologic data as whether a patient's tongue is moving or vibrating (e.g., whether the patient is snoring), by how much the tongue is moving or vibrating, the direction of motion of the tongue, the rate of motion of the tongue, etc.

In response to any of these determined physiologic data, processor 144 may regulate delivery of power to implant unit 110 based on the determined physiologic data. For example, processor 144 may select parameters for a particular modulation control signal or series of modulation control signals for addressing a specific condition relating to the determined physiologic data. If the physiologic data indicates that the tongue is vibrating, for example, processor 144 may determine that a sleep apnea event is likely to occur and may issue a response by delivering power to implant unit 110 in an amount selected to address the particular situation. If the tongue is in a position blocking the patient's airway (or partially blocking a patient's airway), but the physiologic data indicates that the tongue is moving away from the airway, processor 144 may opt to not deliver power and wait to determine if the tongue clears on its own. Alternatively, processor 144 may deliver a small amount of power to implant unit 110 (e.g., especially where a determined rate of movement indicates that the tongue is moving slowly away from the patient's airway) to encourage the tongue to continue moving away from the patient's airway or to speed its progression away from the airway. The scenarios described are exemplary only. Processor 144 may be configured with software and/or logic enabling it to address a variety of different physiologic scenarios with particularity. In each case, processor 144 may be configured to use the physiologic data to determine an amount of power to be delivered to implant unit 110 in order to modulate nerves associated with the tongue with the appropriate amount of energy.

The disclosed embodiments may be used in conjunction with a method for regulating delivery of power to an implant unit. The method may include determining a degree of coupling between primary antenna 150 associated with external unit 120 and secondary antenna 152 associated with implant unit 110, implanted in the body of a patient. Determining the degree of coupling may be accomplished by processor 144 located external to implant unit 110 and that may be associated with external unit 120. Processor 144 may be configured to regulate delivery of power from the external unit to the implant unit based on the determined degree of coupling.

As previously discussed, the degree of coupling determination may enable the processor to further determine a location of the implant unit. The motion of the implant unit may correspond to motion of the body part where the implant unit may be attached. This may be considered physiologic data received by the processor. The processor may, accordingly, be configured to regulate delivery of power from the power source to the implant unit based on the physiologic data. In alternative embodiments, the degree of coupling determination may enable the processor to determine information pertaining to a condition of the implant unit. Such a condition may include location as well as information pertaining to an internal state of the implant unit. The processor may, according to the condition of the implant unit, be configured to regulate delivery of power from the power source to the implant unit based on the condition data.

In some embodiments, implant unit 110 may include a processor located on the implant. A processor located on implant unit 110 may perform all or some of the processes described with respect to the at least one processor associated with an external unit. For example, a processor associated with implant unit 110 may be configured to receive a control signal prompting the implant controller to turn on and cause a modulation signal to be applied to the implant electrodes for modulating a nerve. Such a processor may also be configured to monitor various sensors associated with the implant unit and to transmit this information back to and external unit. Power for the processor unit may be supplied by an onboard power source or received via transmissions from an external unit.

In other embodiments, implant unit 110 may be self-sufficient, including it's own power source and a processor configured to operate the implant unit 110 with no external interaction. For example, with a suitable power source, the processor of implant unit 110 could be configured to monitor conditions in the body of a subject (via one or more sensors or other means), determining when those conditions warrant modulation of a nerve, and generate a signal to the electrodes to modulate a nerve. The power source could be regenerative based on movement or biological function; or the power sources could be periodically rechargeable from an external location, such as, for example, through induction.

Other embodiments of the present disclosure will be apparent to those skilled in the art from consideration of the specification and practice of the present disclosure.

Additional aspects of the invention are described in the following numbered paragraphs, which are part of the description of exemplary embodiments of the invention. Each numbered paragraph stands on its own as a separate embodiment of the invention.

What is claimed is:

1. A device for treating sleep apnea, and for cooperating with a patch configured for adhesion to convey power from a location external to a subject to an implant beneath the subject's skin, the device comprising:
    a housing configured for selective mounting on a side of the patch, the housing including one or more electrical connectors configured to maintain electrical contact with an electrical portion of an antenna, the electrical portion of the antenna being exposed on the side of the patch for mounting the housing; and
    at least one processor within the housing, wherein the at least one processor is configured to:
    be activated by the selective mounting of the housing on the patch, wherein activation enables the implant to modulate a hypoglossal nerve and thereby cause contraction of a genioglossus muscle;
    after the activation of the at least one processor, cause generation of sub-modulation signals to facilitate placement of the patch on the subject's skin at a position relative to an implant beneath the subject's skin, the sub-modulation signals having a power level below a stimulation threshold for a nerve or nerve tissue;
    discontinue the sub-modulation signals after the placement of the patch at the position relative to the implant beneath the subject's skin;
    delay, for a predetermined amount of time after the activation of the at least one processor and the placement of the patch, generation of modulation signals to thereby delay at least one contraction of a genioglossus muscle until after the subject has had an opportunity to fall asleep; and
    increase one or more parameters of the modulation signals periodically until receiving a feedback signal indicating nerve modulation has occurred.

2. The device of claim 1, wherein the delay extends for at least a calibration period associated with device.

3. The device of claim 1, wherein the delay is of sufficient time duration to enable proper placement of the patch on the subject's skin, the sufficient time duration including at least one of approximately 30 seconds, 1 minute, 2 minutes, 5 minutes, and 10 minutes.

4. The device of claim 1, wherein the predetermined amount of time is zero.

5. The device of claim 1, wherein the delay is of sufficient time duration to enable the subject to fall asleep, the sufficient time duration being between approximately fifteen to ninety minutes.

6. The device of claim 1, wherein the at least one processor is further configured to enable generation of therapeutic control signals for modulating at least one nerve in the subject's body after placement of the patch on the subject's skin.

7. The device of claim 1, wherein the predetermined amount of time is greater than zero.

* * * * *